United States Patent
Carola et al.

(10) Patent No.: US 9,655,828 B2
(45) Date of Patent: May 23, 2017

(54) GLUCURONOLACTONE DERIVATIVES AS SELF-TANNING SUBSTANCES

(71) Applicant: Merck Patent GmbH, Darmstadt (DE)

(72) Inventors: Christophe Carola, Bensheim (DE); Rene Peter Scheurich, Gross-Zimmern (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/770,228

(22) PCT Filed: Jan. 30, 2014

(86) PCT No.: PCT/EP2014/000253
§ 371 (c)(1),
(2) Date: Aug. 25, 2015

(87) PCT Pub. No.: WO2014/127882
PCT Pub. Date: Aug. 28, 2014

(65) Prior Publication Data
US 2016/0008253 A1    Jan. 14, 2016

(30) Foreign Application Priority Data

Feb. 25, 2013 (EP) .................. 13000920

(51) Int. Cl.

| | | |
|---|---|---|
| *A61K 8/49* | (2006.01) | |
| *C07D 493/14* | (2006.01) | |
| *A61K 8/35* | (2006.01) | |
| *A61Q 5/10* | (2006.01) | |
| *A61Q 17/04* | (2006.01) | |
| *D06P 1/00* | (2006.01) | |
| *A61Q 19/04* | (2006.01) | |

(52) U.S. Cl.
CPC .............. *A61K 8/4973* (2013.01); *A61K 8/35* (2013.01); *A61Q 5/10* (2013.01); *A61Q 17/04* (2013.01); *A61Q 19/04* (2013.01); *C07D 493/14* (2013.01); *D06P 1/00* (2013.01)

(58) Field of Classification Search
CPC ...... A61K 8/4973; A61K 8/35; C07D 493/14; A61Q 5/10; A61Q 17/04; A61Q 19/04; D06P 1/00
See application file for complete search history.

(56) References Cited

U.S. PATENT DOCUMENTS

| | | | | |
|---|---|---|---|---|
| 7,842,723 | B2 * | 11/2010 | Gupta ................. | A61K 8/0208 424/70.13 |
| 2013/0115178 | A1 * | 5/2013 | Bicard-Benhamou ... | A61K 8/35 424/59 |
| 2015/0098914 | A1 * | 4/2015 | Carola ................. | A61K 31/34 424/59 |

FOREIGN PATENT DOCUMENTS

| | | |
|---|---|---|
| WO | 2012/010242 A2 | 1/2012 |
| WO | 2013/083225 A1 | 6/2013 |

OTHER PUBLICATIONS

International Search Report dated Apr. 1, 2014 issued in corresponding PCT/EP2014/000253 application (pp. 1-2).

\* cited by examiner

*Primary Examiner* — Sean Basquill
(74) *Attorney, Agent, or Firm* — Millen, White, Zelano and Branigan, P.C.

(57) ABSTRACT

The invention relates to the use of specific glucuronolactone derivatives as self-tanning substances, as tanning enhancers for dihydroxyacetone or for a mixture of self-tanning substances comprising dihydroxyacetone, for modulation of the hue achieved in the case of tanning with dihydroxyacetone or by the mixture or preparation comprising dihydroxyacetone, as contrast-reduction agents or for coloring keratin-containing fibers, and to preparations or compositions for coloring keratin-containing fibers comprising these specific glucuronolactone derivatives.

26 Claims, No Drawings

GLUCURONOLACTONE DERIVATIVES AS SELF-TANNING SUBSTANCES

The invention relates to the use of specific glucuronolactone derivatives as self-tanning substances, as tanning enhancers for dihydroxyacetone or for a mixture of self-tanning substances comprising dihydroxyacetone, for modulation of the hue achieved in the case of tanning with dihydroxyacetone or by the mixture or preparation comprising dihydroxyacetone, as contrast-reduction agents or for colouring keratin-containing fibres, and to preparations or compositions for colouring keratin-containing fibres comprising these specific glucuronolactone derivatives.

The trend away from refined paleness towards "healthy, sporty brown skin" has been uninterrupted for years. In order to achieve a tanned complexion, people expose their skin to sunlight, since this causes pigmentation due to melanin formation. However, the UV radiation in sunlight also has a damaging effect on the skin. Besides acute damage (sunburn), long-term damage occurs on excessive irradiation with light from the UVB region (wavelength 280-320 nm), such as, for example, an increased risk of contracting skin cancer. Excessive exposure to UVB and UVA radiation (wavelength: 320-400 nm) generates highly reactive free-radical species, which multiply further even after termination of the irradiation, and wrinkling and skin ageing occur as a consequence thereof.

Tanning (pigmentation) of the skin offers natural protection against the adverse consequences of sunlight. The epidermis contains individual pigment-forming cells, the melanocytes, besides the basal cells in its lowest layer, the basal layer. UV light stimulates the production of melanin in these cells, which is transported into the kerantinocytes (horny cells), where it becomes visible as a brown skin colour. Melanin protects the cell nuclei against further irradiation and the adverse effects it causes on the cell DNA. It wraps around the cell nucleus like a parasol and thus protects it against harmful UV radiation.

Depending on the chemical composition of the pigments formed biochemically, a distinction is made between brownish-black eumelanin and reddishyellow pheomelanin. The skin hue observed is determined by the ratio of these two types of melanin.

This pigment formation starting from the amino acid tyrosine is initiated predominantly by UVB radiation and is known as "indirect pigmentation". Its development runs over a number of days; the suntan obtained in this way lasts a few weeks. In the case of "direct pigmentation", which commences with the solar irradiation, predominantly colourless melanin precursors are oxidised by UVA radiation to dark-coloured melanin. Since this oxidation is reversible, it results in skin tanning which only lasts briefly.

Much more popular, however, is artificial tanning of the skin which can be achieved by the application of so-called self-tanners.

The classical self-tanners, such as, for example, 1,3-dihydroxyacetone (DHA), can be reacted with the proteins and amino acids of the horny layer of the skin in the sense of a Maillard reaction or via a Michael addition, where polymers which give the skin a brownish hue form via a reaction route which has not yet been clarified completely. This reaction is complete after about 4 to 6 hours. The tan achieved in this way cannot be washed off and is only removed with the normal skin desquamation.

DHA is a water-soluble crystalline solid which is unstable under neutral to basic conditions. This instability is also accompanied by the development of cosmetically undesired malodours.

A problem which can frequently occur on use with self-tanner substances, in particular with 1,3-dihydroxyacetone, is that the tanning of the skin is discoloured towards orange by the dominance of the yellow component.

There also continues to be a demand for dermatologically tolerated skincolouring substances, in particular for combination with dihydroxyacetone, which are suitable for use in cosmetic and/or dermatological preparations or medical devices.

The present invention is concerned with the object of improving the colouring of protein-containing matrices, in particular the colouring of the skin with respect to a more natural hue.

The present invention is likewise concerned with the object of developing tolerated, in particular skin-tolerated dyes for colouring keratin-containing fibres.

Surprisingly, it has been found that the glucuronolactone derivatives of the formula I, as described below, and/or salts, tautomers, stereoisomers and/or solvates thereof, alone are capable of colouring the skin, and/or together with dihydroxyacetone are capable of colouring the skin darker than the self-tanner dihydroxyacetone alone, and/or together with dihydroxyacetone are capable of achieving modulation of the hue to give a more natural shade, and/or are capable of reducing the contrast between relatively strongly coloured and less strongly coloured areas of the skin and/or are also very highly suitable as direct dyes for colouring keratin-containing fibres. This property is surprising inasmuch as the anomeric C atom of the glucuronolactone derivatives of the formula I is in protected form and thus a Maillard reaction in the classical sense cannot be present.

The invention accordingly relates to the use of at least one compound of the formula I

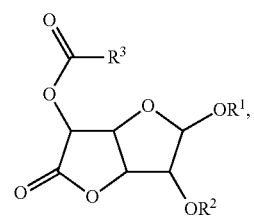

where
$R^1$ and $R^2$ each, independently of one another, denote a straight-chain or branched alkyl group having 1 to 30 C atoms,
and
either $R^1$ or $R^2$ may denote H,
or
$R^1$ and $R^2$ together form an unsubstituted or substituted five-membered ring, which may be substituted
a) by at least one straight-chain or branched alkyl group having 1 to 30 C atoms and/or
b) by at least one aryl group having 6 to 12 C atoms,
where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl,
$R^3$ denotes a straight-chain or branched alkyl group having 1 to 30 C atoms
or
an aryl group having 6 to 12 C atoms, where the aryl group having 6 to 12 C atoms may be substituted by alkyl, vinyl, OH, Oalkyl, $NH_2$, NHalkyl, $N(alkyl)_2$, C(O)alkyl, O—C(O) alkyl and/or C(O)Oalkyl or
a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, NH$_2$, NHalkyl, N(alkyl)$_2$, C(O)alkyl, O—C(O)alkyl and/or C(O)Oalkyl and alkyl denotes a straight-chain or branched alkyl group having 1 to 30 C atoms, and/or salts, tautomers, stereoisomers and/or solvates thereof, including mixtures thereof in all ratios, as self-tanning substance.

The invention accordingly furthermore relates to the use of at least one compound of the formula I, as described above, and/or salts, tautomers, stereoisomers and/or solvates thereof, including mixtures thereof in all ratios, as tanning enhancer for dihydroxyacetone or for a mixture of self-tanning substances comprising dihydroxyacetone.

The invention accordingly furthermore relates to the use of at least one compound of the formula I, as described above, and/or salts, tautomers, stereoisomers and/or solvates thereof, including mixtures thereof in all ratios, for modulation of the hue achieved in the case of tanning with dihydroxyacetone or by the mixture or preparation comprising dihydroxyacetone.

For the purposes of the invention, the compounds of the formula I are defined in such a way that they are also taken to mean pharmaceutically or cosmetically usable derivatives, salts, hydrates, solvates, precursors of the compounds, tautomers and optically active forms (such as, for example, stereoisomers, diastereomers, enantiomers, racemates). Solvates of the compounds are taken to mean adductions of inert solvent molecules onto the compounds which form owing to their mutual attractive force. Solvates are, for example, mono- or dihydrates or alcoholates. Pharmaceutically or cosmetically usable derivatives are taken to mean, for example, the salts and complexes of the compounds according to the invention and also so-called precursors of the compounds. Precursors are taken to mean, for example, compounds of the formula I which have been modified by means of alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61-67 (1995). Any compound which can be converted in vivo into a bioactive agent, i.e. compounds of the formula I, is a precursor in the sense of this invention. Any biologically active compound which results from the in-vivo metabolism of a compound according to the invention is a metabolite in the sense of the present invention. The compounds of the formula I can have one or more chiral centres and can therefore occur in various stereoisomeric forms. The formula I includes all these forms. If the starting compound employed is D-glucuronic acid 3,6-lactone, the compounds of the formula I, as described above, principally have the stereochemistry as depicted in formula I-1, where R$^1$, R$^2$ and R$^3$ have a meaning indicated above.

The formula I-1 visualizes the diastereomers of the formula I, based on α-D-(+)-glucuronic acid 3,6-lactone and β-D-(+)-glucuronic acid 3,6-lactone:

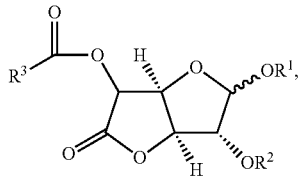

I-1 where R$^1$, R$^2$ and R$^3$ have a meaning indicated above.

A base of the formula I can be converted into the associated acid-addition salt using an acid, for example by reaction of equivalent amounts of the base and acid in an inert solvent, such as ethanol, and subsequent evaporation. Suitable acids for this reaction are, in particular, those which give physiologically acceptable salts.

On the other hand, compounds of the formula I can be converted into the corresponding metal salts, in particular alkali-metal or alkaline-earth metal salts, or into the corresponding ammonium salts using bases (for example sodium hydroxide or carbonate or potassium hydroxide or carbonate).

Preference is given to the use of the compounds of the formula I, as described above or described as preferred below including the stereoisomeric forms. Particular preference is given to the use of the compounds of the formula I-1, where R$^1$, R$^2$ and R$^3$ have a meaning indicated above or below.

The compounds of the formula I, as described above or described as preferred below, and/or salts, tautomers, stereoisomers and/or solvates thereof, including mixtures thereof in all ratios are able to tan the skin.

In the case of a combination of DHA with at least one of the compounds of the formula I, as described above, in particular with at least one preferred compounds of the formula I or of the formula I-1, in which R$^3$ denotes an unsubstituted or substituted aryl group having 6 to 12 C atoms or an alkenyl group having 2 to 30 C atoms, which may be substituted by an unsubstituted or substituted aryl group having 6 to 12 C atoms, for use in cosmetic formulations which serve for colouring the skin, a preferred red shift of the hue achieved is observed.

Thus, with dihydroxyacetone or a mixture of self-tanning substances comprising dihydroxyacetone as self-tanner and on use of at least one compound of the formula I, as described above or described as preferred, self-tanning of the skin can be carried out with a coloration having a natural appearance, without an undesired yellow cast of the coloured skin.

Throughout the document, the term self-tanner or self-tanning substance or self-tanner substance is used synonymously. These terms denote a substance which colours the skin.

The principle of colouring with formation of melanoids is the basic colouring principle of the self-tanning substances, which react in the sense of a Maillard reaction or via a Michael addition. Although the compounds of the formula I do not, according to knowledge to date, have a tanning mechanism of this type, the colouring capacity of classical Maillard self-tanning substances of this type can nevertheless surprisingly be enhanced through the use of at least one compound of the formula I, as described above.

The use of compounds of the formula I, as described above or described as preferred, enables the colouring process with dihydroxyacetone to be enhanced and/or the hue achieved to be improved. Accordingly, a tanning enhancer is taken to mean a compound of the formula I which is capable, on colouring of the skin with dihydroxyacetone, of achieving an optionally darker, hue, which may also be shifted more towards red, than a hue which is achieved with dihydroxyacetone or a mixture of self-tanning substances comprising dihydroxyacetone alone.

In addition, compounds of the formula I, as described above or preferably described, can have a contrast-reduction effect, which reduces an uneven skin coloration in use with dihydroxyacetone or a mixture of self-tanning substances comprising dihydroxyacetone and thus reduces the contrast between relatively strongly coloured and less strongly coloured areas of the skin. An uneven skin coloration of this type may arise through uneven pigmentation and/or a different distribution of the horny skin. A contrast-reduction agent is accordingly a substance which reduces an uneven skin coloration by reducing the contrast between relatively strongly coloured and less strongly coloured areas of the skin.

The invention accordingly furthermore relates to the use of at least one compound of the formula I, as described above or described as preferred, and/or salts, tautomers, stereoisomers and/or solvates thereof, including mixtures thereof in all ratios, as contrast-reduction agent.

In combination with dihydroxyacetone, colouring of the skin with more natural skin colorations, in particular shifted into the red colour region, is achieved, with an advantageous reduction in contrast of unevenly coloured skin areas additionally being possible. Moreover, drying-out of the skin can likewise advantageously be reduced by compounds of the formula I, as described above, on application to the skin.

A reduction in contrast can therefore be achieved, in particular, by preparations in which combinations according to the invention of dihydroxyacetone or a mixture of self-tanning substances comprising dihydroxyacetone and at least one compound of the formula I, as described above or described as preferred, are additionally combined with a substance which inhibits the biochemical formation of melanin. The combination of tanning mixtures, with melanogenesis-inhibiting substances has the effect that skin areas which are already hyperpigmented lose their high melanin concentrations and the hue generated by the colorant on the skin surface imposes itself over a large area.

Suitable for combination are melanogenesis inhibitors, such as, for example, hydroquinone, niacinamide, arbutin, alpha-arbutin, beta-arbutin, deoxyarbutin, vitamin C, ascorbyl palmitate, magnesium ascorbyl phosphate, sodium ascorbyl phosphate, azelaic acid, potassium 4-methoxysalicylate, trans-4-(aminomethyl)cyclohexanecarboxylic acid (tranexamic acid), liquorice extract, ascorbyl glucoside, 3-O-ethylascorbyl ether, 2-O-ethylascorbyl ether, kojic acid, kojic acid dipalmitate, resorcinol, glutathione, cysteine, mulberry tree extract, hydrogen peroxide, zinc peroxide, sodium peroxide, benzoyl peroxide, glucosamine, aloesin, oleic acid 4-isopropyl-catechol, emblica, glycolic acid, ellagic acid, ferulaic acid, resveratrol, oxyresveratrol, quercetin, kaempferol, gallic acid, hesperidin, p-coumaric acid, epicatechol gallate, epigallocatechol gallate, α-hydroxycarboxylic acids (for example lactic acid, salicylic acid, malic acid), α-tocopherol, (E)-3-(4-methoxyphenyl)acrylic acid (R)-2-((R)-3,4-dihydroxy-5-oxo-2,5-dihydro-furan-2-yl)-2-hydroxyethyl ester or 1-[4-(1,1-dimethylethyl)phenyl]-3-(4-methoxyphenyl)-1,3-propanediol. Preferred melanogenesis inhibitors are ascorbic acid and derivatives thereof, niacinamide, emblica, ellagic acid, mulberry tree extract, kojic acid, liquorice extract, rucinol, hydroquinone, azelaic acid, arbutin, magnesium ascorbyl phosphate (E)-3-(4-methoxyphenyl)acrylic acid (R)-2-((R)-3,4-dihydroxy-5-oxo-2,5-dihydrofuran-2-yl)-2-hydroxyethyl ester or 1-[4-(1,1-dimethylethyl)phenyl]-3-(4-methoxyphenyl)-1,3-propanediol.

It has furthermore surprisingly been found that the compounds of the formula I, as described above or described as preferred, are very highly suitable as direct dyes for colouring keratin-containing fibres.

The invention therefore likewise relates to the use of at least one compound of the formula I

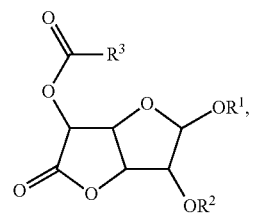

where
$R^1$ and $R^2$ each, independently of one another, denote a straight-chain or branched alkyl group having 1 to 30 C atoms,
and
either $R^1$ or $R^2$ may denote H,
or
$R^1$ and $R^2$ together form an unsubstituted or substituted five-membered ring, which may be substituted
a) by at least one straight-chain or branched alkyl group having 1 to 30 C atoms and/or
b) by at least one aryl group having 6 to 12 C atoms,
where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl,
$R^3$ denotes a straight-chain or branched alkyl group having 1 to 30 C atoms
or
an aryl group having 6 to 12 C atoms, where the aryl group having 6 to 12 C atoms may be substituted by alkyl, vinyl, OH, Oalkyl, $NH_2$, NHalkyl, $N(alkyl)_2$, C(O)alkyl, O—C(O) alkyl and/or C(O)Oalkyl or
a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl
and
alkyl denotes a straight-chain or branched alkyl group having 1 to 30 C atoms,
and/or salts, tautomers, stereoisomers and/or solvates thereof, including mixtures thereof in all ratios, for colouring keratin-containing fibres.

The invention furthermore relates to the use of the compounds of the formula I, as described above or described as preferred, and/or salts, tautomers, stereoisomers and/or solvates thereof, including mixtures thereof in all ratios, as direct dye for the preparation of a composition for colouring keratin-containing fibres.

Keratin-containing fibres are preferably taken to mean human hair, nails, wool, pelts or feathers. However, the compounds according to the invention are in principle also suitable for colouring other natural fibres, such as, for example, cotton, jute, sisal, linen or silk, or for colouring modified natural fibres, such as, for example, regenerated cellulose, nitro-, alkyl- or hydroxyalkyl- or acetylcellulose. The keratin-containing fibre is particularly preferably human hair.

The term "colouring of keratin-containing fibres" used in accordance with the invention encompasses any form of colour change of the fibres. In particular, the colour changes covered by the terms tinting, bleaching, oxidative colouring, semipermanent colouring, permanent colouring and temporary colouring are encompassed. Likewise, colour changes may occur which have a paler colour result compared with the starting colour, such as, for example, bleaching. The term "colouring of keratin-containing fibres" is preferably taken to mean tinting or temporary, semipermanent or permanent colouring.

A straight-chain or branched alkyl group having 1 to 10 C atoms is, for example, methyl, ethyl, isopropyl, propyl, butyl, sec-butyl or tert-butyl, pentyl, 1-, 2- or 3-methylbutyl, 1,1-, 1,2- or 2,2-dimethylpropyl, 1-ethylpropyl, n-hexyl, n-heptyl, n-octyl, n-nonyl or n-decyl.

A straight-chain or branched alkyl group having 1 to 30 C atoms includes the group of straight-chain or branched alkyl group having 1 to 10 C atoms described above and undecanyl, dodecanyl, tridecanyl, tetradecanyl, pentadecanyl, hexadecanyl, heptadecanyl, octadecanyl, nonadecanyl, eicosanyl, heneicosanyl, docosanyl, tricosanyl, tetracosanyl, pentacosanyl, hexacosanyl, heptacosanyl, octacosanyl, nonacosanyl and triacontanyl.

The term "alkyl" used here denotes a straight-chain or branched alkyl group having 1 to 30 C atoms, preferably an alkyl group having 1 to 10 C atoms, particularly preferably methyl, ethyl, isopropyl, n-propyl or n-butyl.

The term Oalkyl is known to the person skilled in the art and denotes a straight-chain or branched alkoxy group having 1 to 30 C atoms. The names can be derived from the names of the alkyl group in which the ending -oxy is appended. The alkoxy group Omethyl is, for example, methyloxy.

The term NHalkyl denotes a monoalkylated amino group, where the alkyl group may be straight-chain or branched and has 1 to 30 C atoms.

The term $N(alkyl)_2$ accordingly denotes a dialkylamino group, where the alkyl group may in each case, independently of one another, be straight-chain or branched and have 1 to 30 C atoms.

The term C(O)alkyl denotes a —C(=O)-alkyl group, where alkyl has a meaning indicated above.

The term O—C(O)alkyl denotes an —O—C(=O)-alkyl group, where alkyl has a meaning indicated above.

The term C(O)Oalkyl denotes a —C(=O)—O-alkyl group, where alkyl has a meaning indicated above.

A straight-chain or branched alkenyl having 2 to 30 C atoms, where a plurality of double bonds may also be present, is, for example, ethenyl, allyl, 2- or 3-butenyl, isobutenyl, sec-butenyl, furthermore 4-pentenyl, isopentenyl, hexenyl, heptenyl, octenyl, —$C_9H_{17}$, —$C_{10}H_{19}$ to —$C_{30}H_{49}$; preferably ethenyl, allyl, 2- or 3-butenyl, isobutenyl, sec-butenyl, 4-pentenyl, isopentenyl, hexenyl or decenyl. Particularly preferred alkenyl groups are ethenyl, 2- or 3-butenyl.

An aryl group having 6 to 12 C atoms denotes phenyl, naphthyl, anthracenyl or phenanthryl, which may be substituted by alkyl, OH, Oalkyl, $NH_2$, NH-alkyl, $N(alkyl)_2$, C(O)alkyl, O—C(O)-alkyl or C(O)-Oalkyl. The aryl group is preferably phenyl which is unsubstituted or substituted by alkyl, OH, Oalkyl, $NH_2$, NH-alkyl, $N(alkyl)_2$, C(O)alkyl, O—C(O)-alkyl or C(O)-Oalkyl.

In the compounds of the formula I or of the formula I-1, $R^1$ and $R^2$ preferably together form a five-membered ring, which is substituted by two independent straight-chain or branched alkyl groups having 1 to 10 C atoms.

In an embodiment of the invention, particular preference is given to the use of compounds of the formula I and/or salts, tautomers, stereoisomers and/or solvates thereof, including mixtures thereof, which conform to the formula IA,

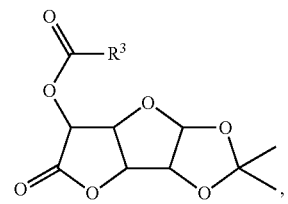

IA where $R^3$ denotes a straight-chain or branched alkyl group having 1 to 30 C atoms or an aryl group having 6 to 12 C atoms, where the aryl group having 6 to 12 C atoms may be substituted by alkyl, vinyl, OH, Oalkyl, $NH_2$, NHalkyl, $N(alkyl)_2$, C(O)alkyl, O—C(O)alkyl and/or C(O)Oalkyl or a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl and alkyl denotes a straight-chain or branched alkyl group having 1 to 30 C atoms.

The formula IA-1 visualizes the diastereomers of the formula IA, based on α-D-(+)-glucuronic acid 3,6-lactone and β-D-(+)-glucuronic acid 3,6-lactone:

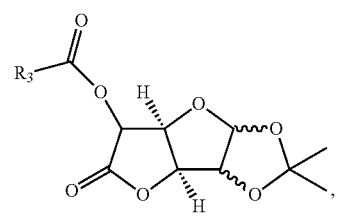

IA-1 where $R^3$ has a meaning indicated above.

The substituent $R^3$ in compounds of the formula I, I-1, IA or IA-1 preferably denotes an aryl group having 6 to 12 C atoms, where the aryl group having 6 to 12 C atoms may be substituted by alkyl, vinyl, OH, Oalkyl, $NH_2$, NHalkyl, $N(alkyl)_2$, C(O)alkyl, O—C(O)alkyl and/or C(O)Oalkyl or a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl.

The substituent $R^3$ in compounds of the formula I, I-1, IA or IA-1 particularly preferably denotes a phenyl group, which is unsubstituted or substituted by alkyl, vinyl, OH, Oalkyl, $NH_2$, NHalkyl, $N(alkyl)_2$, C(O)alkyl, O—C(O)alkyl and/or C(O)Oalkyl or a straight-chain or branched alkenyl group having 2 to 30 C atoms, which is substituted by a phenyl group, where the phenyl group is unsubstituted or substituted by alkyl, OH, Oalkyl, $NH_2$, NHalkyl, $N(alkyl)_2$, C(O)alkyl, O—C(O)alkyl and/or C(O)Oalkyl.

In an embodiment of the invention, very particular preference is given to compounds of the formula IB,

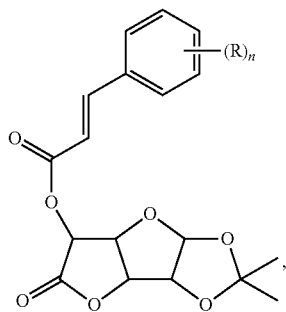

where n denotes 0, 1, 2, 3, 4 or 5 and

R in each case, independently of one another, denotes alkyl, OH, Oalkyl, $NH_2$, NHalkyl, $N(alkyl)_2$, C(O)alkyl, O—C(O)alkyl and/or C(O)Oalkyl and alkyl denotes a straight-chain or branched alkyl group having 1 to 30 C atoms.

The compounds of the formula IB are preferably in the E geometry.

The formula IB-1 visualizes the diastereomers of the formula I-B, based on α-D-(+)-glucuronic acid 3,6-lactone and β-D-(+)-glucuronic acid 3,6-lactone:

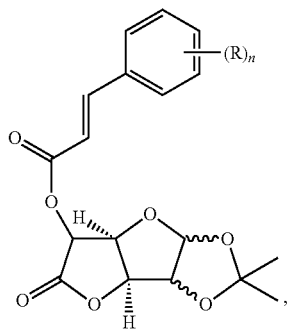

where R and n have a meaning indicated above.

The substituent R in compounds of the formula IC or IC-1 is preferably OH or Oalkyl. The variable n is preferably 0, 1, 2 or 3.

The compounds of the formula IB-1 are preferably in the E geometry.

In an embodiment of the invention, very particular preference is given to compounds of the formula IC,

IC

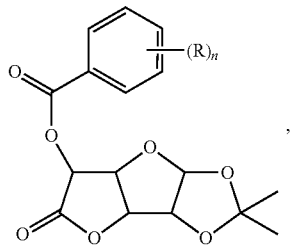

where n denotes 0, 1, 2, 3, 4 or 5 and

R in each case, independently of one another, denotes alkyl, OH, Oalkyl, $NH_2$, NHalkyl, $N(alkyl)_2$, C(O)alkyl, O—C(O)alkyl and/or C(O)Oalkyl and alkyl denotes a straight-chain or branched alkyl group having 1 to 30 C atoms.

The formula IC-1 visualizes the diastereomers of the formula I-C, based on α-D-(+)-glucuronic acid 3,6-lactone and β-D-(+)-glucuronic acid 3,6-lactone:

IC-1

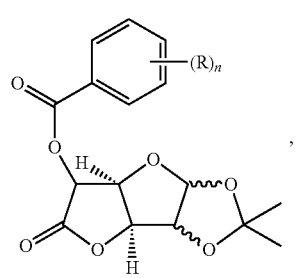

where R and n have a meaning indicated above.

The substituent R in compounds of the formula IC or IC-1 is preferably OH or Oalkyl. The variable n is preferably 0, 1, 2 or 3.

Preferred individual compounds of the formula I are compounds (Ia) to (Iq):

(Ia)

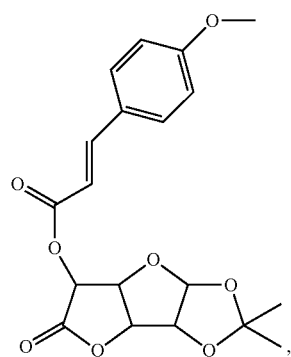

(Ib)

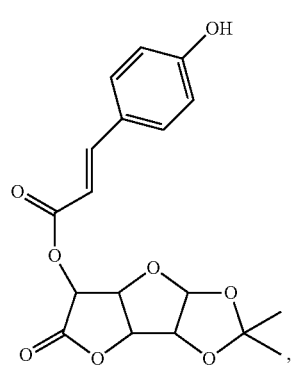

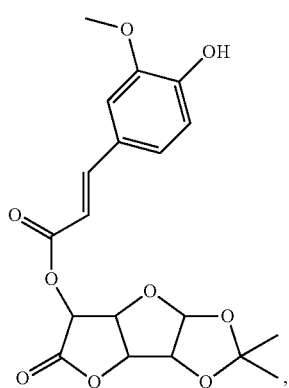
,
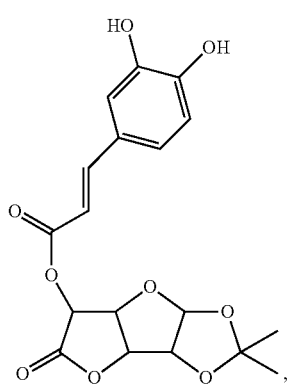
,
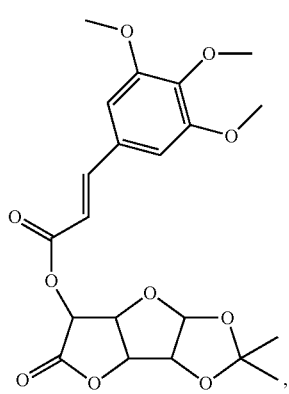
,
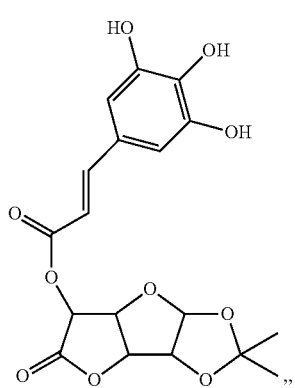
,
(Ic)
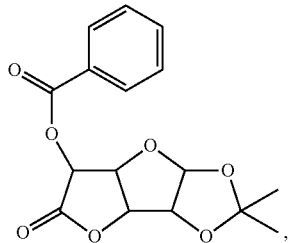
,
(Ih)
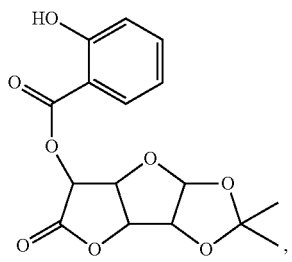
,
(Ii)
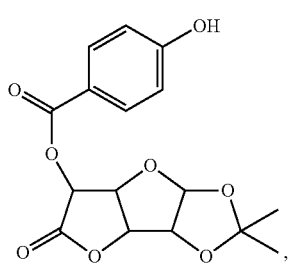
,
(Ij)
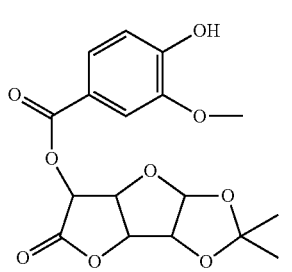
,
(Ik)
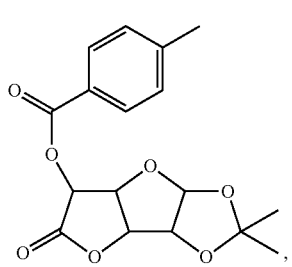
,
(Im)
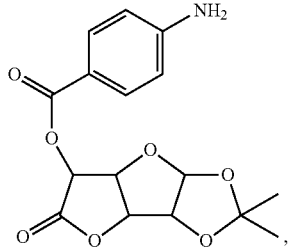
,

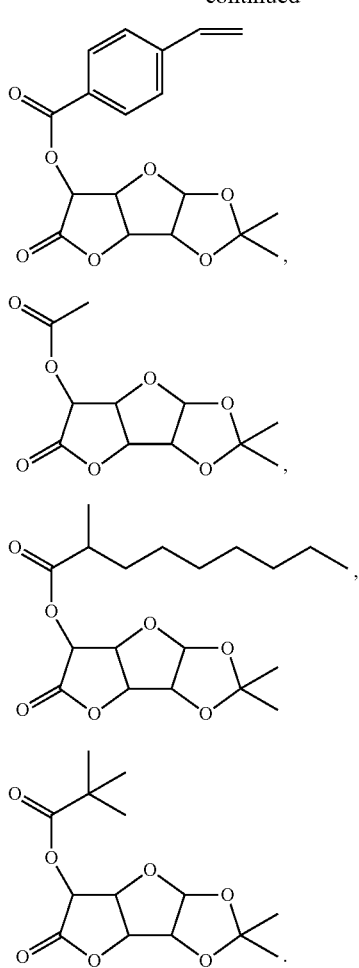

The individual compounds are preferably diastereomers and can likewise be described in accordance with the stereochemistry of the formula I-1.

It is of course possible to vary the colour of the keratin-containing fibres to be achieved through the choice of the substitution of the aryl group in the compounds of the formula I. The stronger, for example, the aromaticity of the corresponding compound of the formula I, the darker is the expected colouring result.

Particular preference is given in accordance with the invention to the use of the compounds of the formulae (Ia) to (Ik), where compounds (Ia) and (Ig) are particularly preferred.

Advantageous self-tanners which can be employed in a dihydroxyacetone-containing mixture or preparation are, inter alia:
glycerolaldehyde, hydroxymethylglyoxal, γ-dialdehyde, erythrulose, 6-aldo-D-fructose, ninhydrin, 5-hydroxy-1,4-naphtoquinone (juglone) or 2-hydroxy-1,4-naphtoquinone (lawsone) or a mixture of the said compounds. Erythrulose is particularly preferably employed in the dihydroxyacetone-containing mixture.

The at least one compound of the formula I, I-1, IA, IA-1, IB or IC, as described above or described as preferred, can also be used in accordance with the invention together with a mixture of self-tanning substances comprising at least dihydroxyacetone and a further self-tanner selected from the above-mentioned group. By way of example, the mixture to be used in accordance with the invention consists of dihydroxyacetone and at least one further self-tanning substance, as described above. This mixture can then be combined in accordance with the invention with at least one compound of the formula I, I-1, IA, IA-1, IB or IC and employed in cosmetic, dermatological or pharmaceutical preparations, as described below.

Very particular preference is given to the use of dihydroxyacetone with at least one compound of the formula I, I-1, IA, IA-1, IB, IB-1, IC or IC-1 without further self-tanning substances from the above-mentioned group of self-tanning substances.

The invention furthermore relates to the compounds of the formula IB,

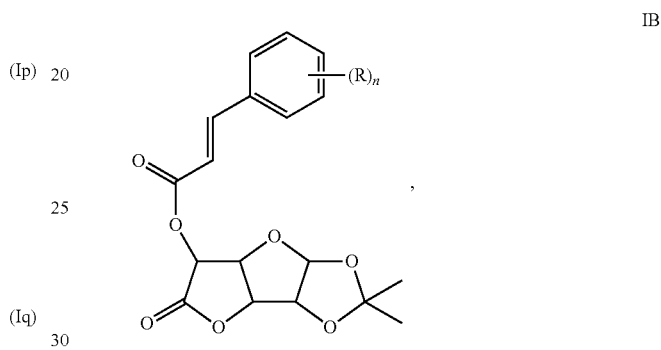

where n denotes 0, 1, 2, 3, 4 or 5 and

R in each case, independently of one another, denotes alkyl, OH, Oalkyl, $NH_2$, NHalkyl, $N(alkyl)_2$, C(O)alkyl, O—C(O)alkyl and/or C(O)Oalkyl and alkyl denotes a straight-chain or branched alkyl group having 1 to 30 C atoms and/or salts, tautomers, stereoisomers and/or solvates thereof, including mixtures thereof in all ratios.

In the compounds of the formula IB or of the formula IB-1, as described above, the term "alkyl" is preferably a straight-chain or branched alkyl group having 1 to 10 C atoms.

In the compounds of the formula IB or of the formula IB-1, as described above, R is preferably OH and/or Oalkyl.

In the compounds of the formula IB or of the formula IB-1, as described above, n is preferably 0, 1, 2 or 3.

The invention furthermore relates to the compounds

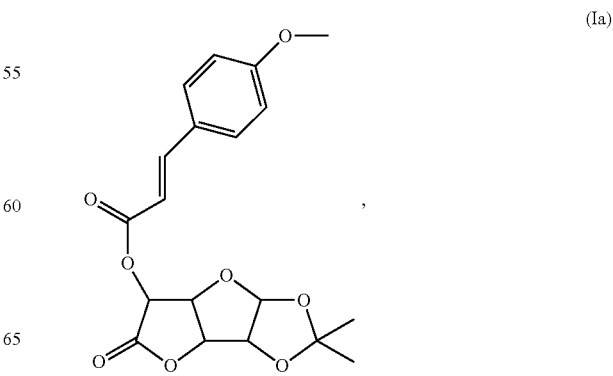

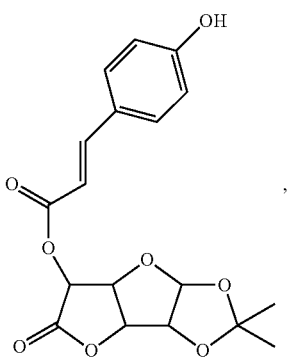
(Ib)

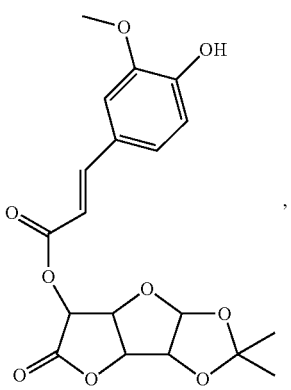
(Ic)

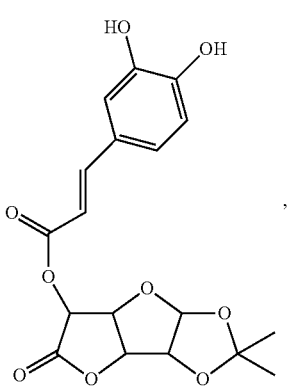
(Id)

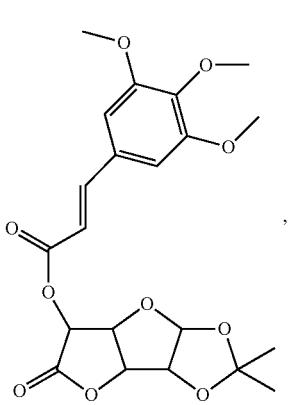
(Ie)

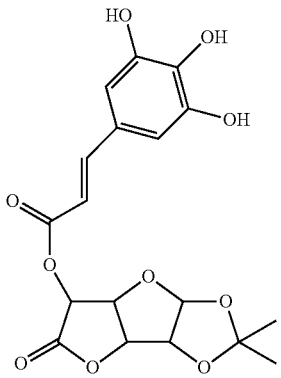
(If)

The compounds of the formula I, I-1, IA, IA-1, IC or IC-1 as described above, and also the starting materials for their preparation are in some cases commercially available or are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

In general, glucuronolactone of the formula II or II-1 or, for compounds of the formula IA, IA-1, IB, IB-1, IC or IC-1, glucuronolactone acetonide of the formula III or III-1,

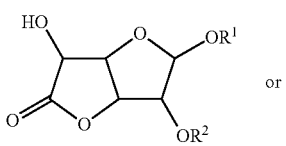
II or

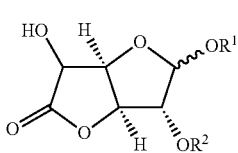
II-1

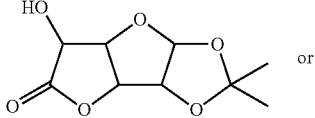
III or

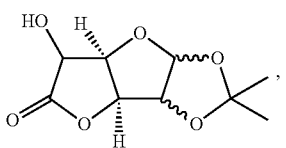
III-1 is the suitable starting material for the compounds of the formula I or formula I-1, as described above or described as preferred.

The compounds of the formula III or III-1 in which $R^1$ and $R^2$ together form a five-membered ring are formed, for example, by (Lewis) acid-catalysed reaction of glucuronolactone with acetone.

The synthesis of compounds of the formula II or II-1 in which $R^1$ and $R^2$ each, independently of one another, denote H or a a straight-chain or branched alkyl group having 1 to 30 C atoms, with the condition that either $R^1$ or $R^2$ can be H, as described above, is carried out by reaction of glucuronolactone with a corresponding alcohol. The reaction is generally carried out with acid catalysis. The precise reaction conditions of these etherifications are adequately known to the person skilled in the art of synthesis. The kinetics of the two OH groups in the glucuronolactone or the compound of the formula II or of the formula II-1 are different, meaning that the etherification can be controlled correspondingly by metered addition and protecting-group chemistry.

The introduction of the substituent $R^3$ into the compounds of the formula I, I-1, IA, IA-1, IB, IB-1, IC or IC-1 is carried out by an esterification. The starting materials of the formulae II, II-1, III or III-1 are reacted with an acid chloride $R^3$—C(=O)—Cl, where $R^3$ has a meaning given above or given as preferred, utilising the Schotten-Baumann reaction. The esterification is generally carried out in the presence of bases, such as, for example, triethylamine or pyridine. In the so-called Einhorn variant, dimethylaminopyridine is additionally added for activation. Besides the use of the acid chlorides, as described above, it is also possible to use acid bromides or anhydrides or active esters of the acid $R^3$—C(=O)—OH. Suitable reaction conditions for esterifications with the aid of active esters is described in Esterification: Methods, Reactions, and Applications, Author: Prof. Dr. Junzo Otera, Wiley-VCH Verlag GmbH & Co.KGaA, ISBN 9783527304905, in particular in Chapter 1, the contents of which in this respect expressly also belong to the disclosure content of the present application.

An alternative process for the preparation of the compounds of the formula I, I-1, IA, IA-1, IB, IB-1, IC or IC-1 is the transesterification from methyl esters of the acids of the formula $R^3$—C(=O)—OH by the method of K. Mori et al, Tetrahedron Lett. 1973, 14, 790-791. The starting materials of the formulae II, II-1, III or III-1 are employed in excess here, and a catalytic amount of cyanide ions is used.

An alternative process for the preparation of the compounds of the formula I, I-1, IA, IA-1, IB, IB-1, IC or IC-1 consists in the reaction of the carboxylic acid methyl ester of the desired aromatic component in the presence of the acetylated form of the glucuronolactone acetonide under the influence of an alcoholate base in accordance with the general reaction scheme Ar stands for the substituent $R^3$, which denotes an aryl group having 6 to 12 C atoms, where the aryl group having 6 to 12 C atoms may be substituted by alkyl, vinyl, OH, Oalkyl, $NH_2$, NHalkyl, $N(alkyl)_2$, C(O)alkyl, O—C(O)alkyl and/or C(O)Oalkyl or a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl.

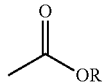

in the scheme indicated above denotes

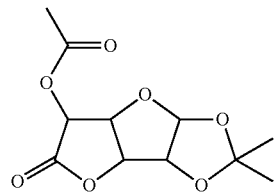

The invention furthermore also relates to a process for the preparation of compounds of the formula IB,

IB

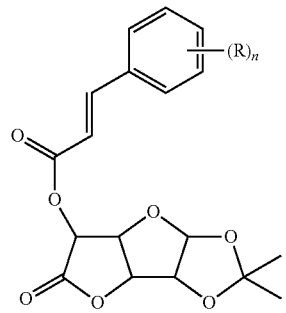

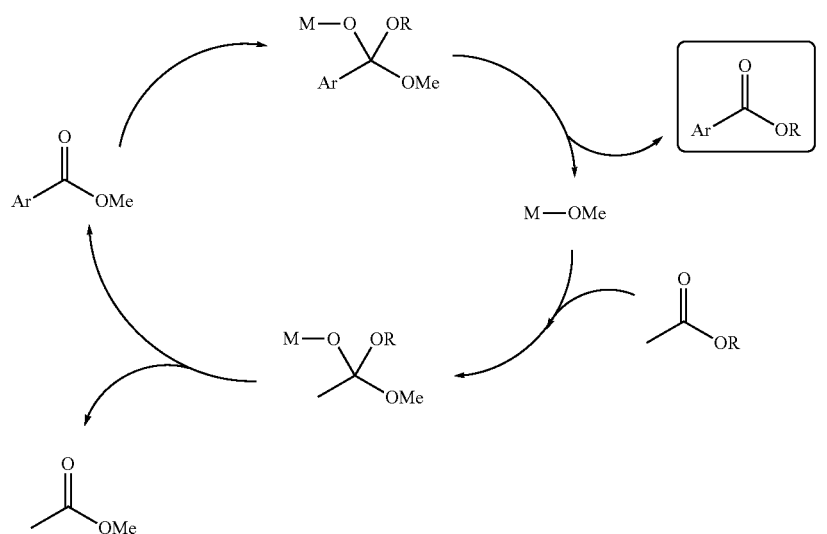

M = Li, Na, K, Rb where
n denotes 0, 1, 2, 3, 4 or 5 and
R in each case, independently of one another, denotes alkyl, OH, Oalkyl, $NH_2$, NHalkyl, $N(alkyl)_2$, C(O)alkyl, O—C(O)alkyl and/or C(O)Oalkyl and alkyl denotes a straight-chain or branched alkyl group having 1 to 30 C atoms and/or salts, tautomers, stereoisomers and/or solvates thereof, including mixtures thereof in all ratios,
characterised in that an active ester, an acid chloride, an acid bromide or methyl ester of the acid of the formula IV, where R and n have a meaning indicated above or meaning preferably indicated,

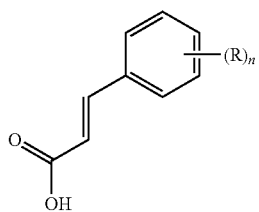

IV is reacted with a compound of the formula III

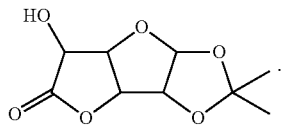

III

The corresponding general comments on the synthesis of the compounds of the formula I also apply in the case of this process.

The invention furthermore relates to preparations comprising a compound of the formula IB, as described above or described as preferred or a compound of the formulae (Ia) to (If).

The preparation preferably comprises the at least one compound of the formula IB or IB-1, as described above or described as preferred, in an amount of 0.01 to 20% by weight, particularly preferably in an amount of 0.5 to 15% by weight and very particularly preferably in an amount of 1 to 8% by weight, based on the total amount of the preparation.

The invention furthermore relates to preparations comprising dihydroxyacetone (DHA) and at least one compound of the formula I, as described above or described as preferred.

The invention furthermore relates to preparations comprising dihydroxyacetone (DHA) and at least one compound of the formula I-1, IA, IA-1, IB, IB-1, IC or IC-1, as described above or described as preferred.

The preparation preferably comprises at least dihydroxyacetone in an amount of 0.01 to 20% by weight, particularly preferably in an amount of 0.5 to 15% by weight and very particularly preferably in an amount of 1 to 8% by weight, based on the total amount of the preparation.

The preparation preferably comprises the at least one compound of the formula I, I-1, IA, IA-1, IB, IB-1, IC or IC-1, as described above or described as preferred, in an amount of 0.01 to 20% by weight, particularly preferably in an amount of 0.5 to 15% by weight and very particularly preferably in an amount of 1 to 8% by weight, based on the total amount of the preparation.

The preparations here are usually preparations which can be applied topically, for example cosmetic or dermatological formulations or medical devices. In this case, the preparations comprise a cosmetically or dermatologically suitable vehicle and, depending on the desired property profile, optionally further suitable ingredients. In the case of pharmaceutical preparations, the preparations in this case comprise a pharmaceutically tolerated vehicle and optionally further pharmaceutical active compounds. In the case of a medicinal device, a vehicle which is tolerated for the medicinal device is selected.

Can be applied topically in the sense of the invention means that the preparation is applied externally and locally, i.e. that the preparation must be suitable for, for example, application to the skin.

In the sense of the present invention, the term composition or formulation is also used synonymously alongside the term preparation.

The preparations may include or comprise, essentially consist of or consist of the said requisite or optional constituents. All compounds or components which can be used in the preparations are either known and commercially available or can be synthesised by known processes.

Further preferred combinations of embodiments are disclosed in the claims.

Particular preference is given in accordance with the invention to cosmetic preparations.

The preparations may preferably comprise assistants, such as, for example, cosmetic oils (for example Caprylic/Capric Triglycerides, C12-15 Alkyl Benzoate, isopropyl myristate, Arylalkyl Benzoate, such as, for example, phenethyl benzoate (X-Tend 226) or oil components of the Cosmacol brand, such as Dimyristyl Tartrate, Tri C14-C15 Alkyl Citrate, C12-C13 Alkyl Lactate, Tridecyl Salicylate, C12-C13 Alkyl Octanoate, C12-C13 Alkyl Malate, C12-C13 Alkyl Citrate, C12-C13 Alkyl Tartrate), or polar-protic assistants (for example propylene glycol, glycerol, isopropanol, ethanol) or so-called solubilisers (for example butylphthalimides, isopropylphthalimides, dimethylisosorbides). Very particularly preferred cosmetic oils are C12-C13 Alkyl Lactate, commercially available as Cosmacol ELI, and phenethyl benzoate, commercially available as X-Tend 226.

Preparations having self-tanner properties, in particular those which comprise dihydroxyacetone, tend towards malodours on application to the human skin, which are thought to be caused by degradation products of dihydroxyacetone itself or by products of side reactions and which are regarded as unpleasant by some users. It has been found that these malodours are prevented on use of formaldehyde scavengers and/or flavonoids. The preparation according to the invention comprising at least one compound of the formula I, I-1, IA, IA-1, IB, IB-1, IC or IC-1, as described above or described as preferred, and the individual compounds and at least one self-tanner, can therefore preferably also comprise formaldehyde scavengers and optionally flavonoids for improving the odour.

However, the compounds of the formula I, I-1, IA, IA-1, IB, IB-1, IC or IC-1 claimed for preparations according to the invention, as well as the corresponding individual compounds, may also themselves contribute to the improvement in odour. In particular, the compounds of the formula I, I-1, IA, IA-1, IB, IB-1, IC or IC-1, as described above, are distinguished by the fact that they do not develop malodours on storage in a preparation.

The formaldehyde scavenger is preferably selected from the group alkali metal, alkaline-earth metal or ammonium disulfite. Particular preference is given to a preparation which comprises, in combination DHA Plus, a mixture of DHA, sodium disulfite and magnesium stearate.

DHA Plus is a product mixture which comprises sodium metabisulfite, synonymous with $Na_2S_2O_5$ or INCI: sodium disulfite, for the masking, elimination or neutralisation of formaldehyde. The addition of sodium metabisulfite in finished formulations results in significant reduction or suppression of the unpleasant odour. DHA Plus is marketed by Merck, Darmstadt.

The preparation according to the invention, as described above, comprising at least one compound of the formula I, I-1, IA, IA-1, IB, IB-1, IC or IC-1, as described above or described as preferred, may particularly preferably comprise flavonoids for improving the odour and optionally for accelerating tanning.

The flavonoid here additionally acts as stabiliser for the self-tanner or the self-tanning substances and/or reduces or prevents or improves storagedependent malodours, which may also arise due to additives or assistants present.

It is preferably a flavonoid in which one or more phenolic hydroxyl groups have been blocked by etherification or esterification. For example, hydroxyethyl-substituted flavonoids, such as, preferably, troxerutin, troxequercetin, troxeisoquercetin or troxeluteolin, and flavonoid sulfates or flavonoid phosphates, such as, preferably, rutin sulfates, have proven to be particularly highly suitable flavonoids here. Particular preference is given in the sense of the use according to the invention to rutin sulfate and troxerutin. Very particular preference is given to the use of troxerutin.

The preferred flavonoids have a non-positively charged flavan skeleton. It is thought that metal ions, such as, for example, $Fe^{2+}/Cu^{2+}$, are complexed by these flavonoids and auto-oxidation processes in the case of fragrances or compounds whose degradation results in malodours are thus prevented or reduced.

Particular preference is given to a preparation which, besides at least one compound of the formula I, I-1, IA, IA-1, IB, IB-1, IC or IC-1, as described above or described as preferred, comprises DHA Rapid. DHA Rapid is a product mixture comprising dihydroxyacetone and troxerutin, from Merck, Darmstadt. This particularly preferred preparation may optionally also comprise a formaldehyde scavenger, for example sodium disulfite.

Corresponding premixes and preparations which comprise formaldehyde scavengers and optionally flavonoids in order to improve the odour on the skin are described in the German patent application DE 10 2007 013 368 A1, the contents of which in this respect expressly also belong to the disclosure content of the present application.

The invention also relates to a process for the preparation of a preparation, as described above, in which at least one compound of the formula I, I-1, IA, IA-1, IB, IB-1, IC or IC-1 as described above or described as preferred, is mixed with a vehicle and optionally with further active compounds or assistants. At least one further self-tanner substance is optionally then added and mixed, and finally dihydroxyacetone is added and mixed. Suitable vehicles and active compounds or assistants are described in detail in the following part.

In the preparations described, which, in accordance with the invention, comprise at least one compound of the formula I, I-1, IA, IA-1, IB, IB-1, IC or IC-1, as described above or described as preferred, and dihydroxyacetone, coloured pigments may furthermore also be present, where the layer structure of the pigments is not limited.

The coloured pigment should preferably be skin-coloured or brownish on use of 0.5 to 5% by weight. The choice of a corresponding pigment is familiar to the person skilled in the art.

Besides the compounds of the formula I, I-1, IA, IA-1, IB, IB-1, IC or IC-1 at least dihydroxyacetone as self-tanning substance and the optional other ingredients, preferred preparations may comprise further organic UV filters, so-called hydrophilic or lipophilic sun-protection filters, which are effective in the UVA region and/or UVB region and/or IR and/or VIS region (absorbers). These substances can be selected, in particular, from cinnamic acid derivatives, salicylic acid derivatives, camphor derivatives, triazine derivatives, β,β-diphenylacrylate derivatives, p-aminobenzoic acid derivatives and polymeric filters and silicone filters, which are described in the application WO-93/04665. Further examples of organic filters are indicated in the patent application EP-A 0 487 404 and WO2009/077356. The said UV filters are usually named in accordance with INCI nomenclature below.

Suitable organic UV-protecting substances can preferably be selected from the following list:
para-aminobenzoic acid and derivatives thereof: PABA, Ethyl PABA, Ethyl dihydroxypropyl PABA, Ethylhexyl dimethyl PABA, for example marketed under the name "Escalol 507" by ISP, Glyceryl PABA, PEG-25 PABA, for example marketed under the name "Uvinul P25" by BASF.

Salicylates: Homosalate, marketed by Merck under the name "Eusolex HMS"; Ethylhexyl salicylate, for example marketed by Symrise under the name "Neo Heliopan OS", Dipropylene glycol salicylate, for example marketed by Scher under the name "Dipsal", TEA salicylate, for example marketed by Symrise under the name "Neo Heliopan TS".

β,β-Diphenylacrylate derivatives: Octocrylene, for example marketed by Merck under the name "Eusolex® OCR", "Uvinul N539" from BASF, etocrylene, for example marketed by BASF under the name "Uvinul N35". Furthermore, for example, methoxycrylene, marketed by Hallstar under the name Solastay S1.

Benzophenone derivatives: Benzophenone-1, for example marketed under the name "Uvinul 400"; Benzophenone-2, for example marketed under the name "Uvinul D50"; Benzophenone-3 or Oxybenzone, for example marketed under the name "Uvinul M40"; Benzophenone-4, for example marketed under the name "Uvinul MS40"; Benzophenone-9, for example marketed by BASF under the name "Uvinul DS-49", Benzophenone-5, Benzophenone-6, for example marketed by Norquay under the name "Helisorb 11", Benzophenone-8, for example marketed by American Cyanamid under the name "Spectra-Sorb UV-24", Benzophenone-12 n-hexyl 2-(4-diethylamino-2-hydroxybenzoyl)benzoate or 2-hydroxy-4-methoxybenzophenone, marketed by Merck, Darmstadt, under the name Eusolex® 4360.

Benzylidenecamphor derivatives: 3-Benzylidenecamphor, for example marketed under the name "Mexoryl SD" by Chimex, 4-Methylbenzylidenecamphor, for example marketed by Merck under the name "Eusolex 6300", benzylidenecamphorsulfonic acid, for example marketed by Chimex under the name "Mexoryl SL", Camphor benzalkonium methosulfate, for example marketed by Chimex under the name "Mexoryl SO", terephthalylidenedicamphorsulfonic acid, for example marketed by Chimex under the name "Mexoryl SX", Polyacrylamidomethylbenzylidenecamphor marketed by Chimex under the name "Mexoryl SW".

Phenylbenzimidazole derivatives: phenylbenzimidazole-sulfonic acid, for example marketed by Merck under the name "Eusolex 232", disodium phenyl dibenzimidazole tetrasulfonate, for example marketed by Symrise under the name "Neo Heliopan AP".

Phenylbenzotriazole derivatives: Drometrizole trisiloxane, for example marketed by Rhodia Chimie under the name "Silatrizole", Methylenebis(benzotriazolyl)tetramethylbutylphenol in solid form, for example marketed by Fairmount Chemical under the name "MIXXIM BB/100", or in micronised form as an aqueous dispersion, for example marketed by BASF under the name "Tinosorb M".

Triazine derivatives: Ethylhexyltriazone, for example marketed by BASF under the name "Uvinul T150", Diethylhexylbutamidotriazone, for example marketed by Sigma 3V under the name "Uvasorb HEB". Further triazine derivatives are by way of example 2,4,6-tris(diisobutyl 4'-aminobenzalmalonate)-s-triazine or 2,4,6-tris(biphenyl)-1,3,5-triazine, or butyl 4-({4-{[4-(butoxycarbonyl)phenyl]amino}-6-[(3-{1,3,3,3-tetramethyl-1-[(trimethylsilyl)oxy]disiloxanyl}propyl)amino]-1,3,5-triazin-2-yl}amino)benzoate, marketed under the name Mexoryl SBS. Structure of Mexoryl SBS:

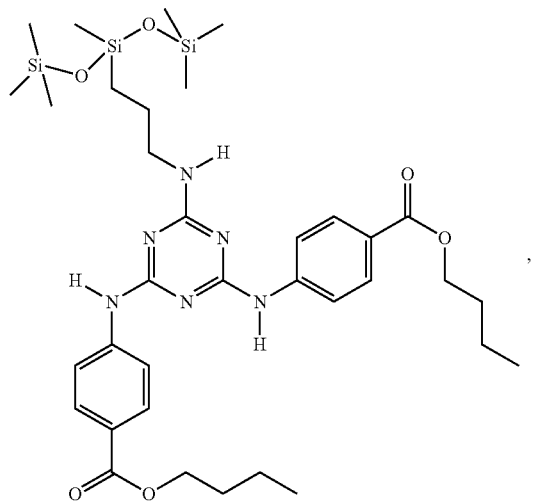 [SMILES: CCCCOC(=O)c1ccc(Nc2nc(NCCC[Si](C)(O[Si](C)(C)C)O[Si](C)(C)C)nc(Nc3ccc(C(=O)OCCCC)cc3)n2)cc1]

and bis-ethylhexyloxyphenol methoxyphenyl triazine, for example marketed by BASF under the name Tinosorb S.

Anthraniline derivatives: Menthyl anthranilate, for example marketed by Symrise under the name "Neo Heliopan MA".

Imidazole derivatives: ethylhexyldimethoxybenzylidene-dioxoimidazoline propionate.

Benzmalonate derivatives: polyorganosiloxanes containing functional benzalmalonate groups, such as, for example, polysilicone-15, for example marketed by Hoffmann LaRoche under the name "Parsol SLX".

4,4-Diarylbutadiene derivatives: 1,1-Dicarboxy(2,2'-dimethylpropyl)-4,4-diphenylbutadiene.

Benzoxazole derivatives: 2,4-bis[5-(1-dimethylpropyl)benzoxazol-2-yl(4-phenyl)imino]-6-(2-ethylhexyl)imino-1,3,5-triazine, for example marketed by Sigma 3V under the name Uvasorb K2A, and mixtures comprising this.

Piperazine derivatives, such as, for example, the compound

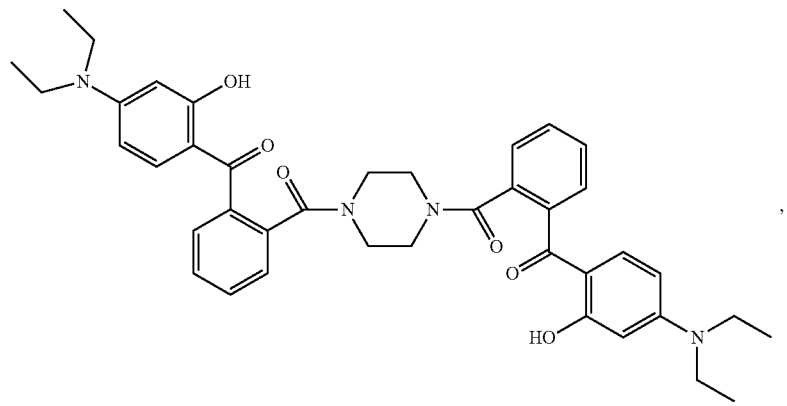 [SMILES: CCN(CC)c1ccc(C(=O)c2ccccc2C(=O)N2CCN(C(=O)c3ccccc3C(=O)c3ccc(N(CC)CC)cc3O)CC2)c(O)c1]

or the UV filters of the following structures

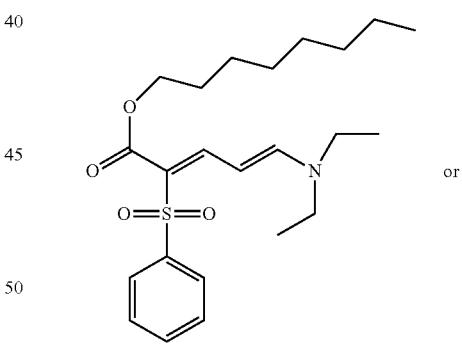

or

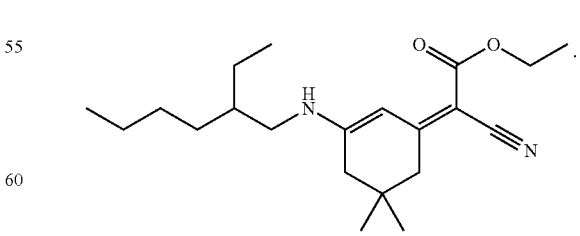

Preference is also given to a combination with UV filters based on polysiloxane copolymers having a random distribution in accordance with the following formula, where, for example, a=1.2; b=58 and c=2.8:

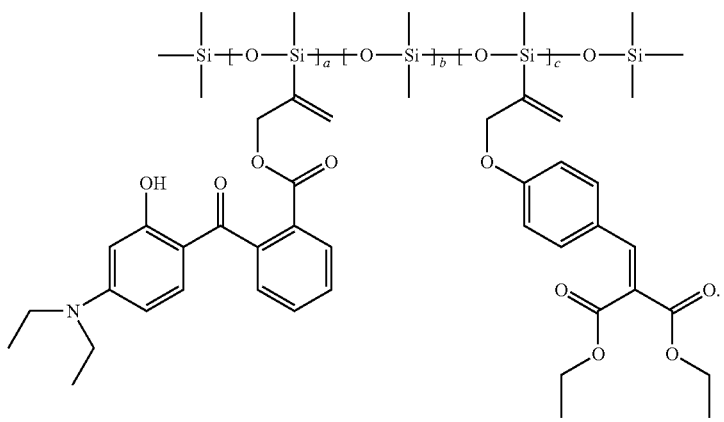

These organic UV filters are generally incorporated into formulations in an amount of 0.01 percent by weight to 20 percent by weight, preferably 1% by weight-10% by weight.

Besides the compounds of the formula I, at least dihydroxyacetone as self-tanning substance and the optional other ingredients, as described above, the preparations may comprise further inorganic UV filters, so-called particulate UV filters.

These combinations with particulate UV filters are possible both as powder and also as dispersion or paste.

Preference is given here both to those from the group of the titanium dioxides, such as, for example, coated titanium dioxide (for example Eusolex® T-2000, Eusolex®T-AQUA, Eusolex®T-AVO, Eusolex®T-OLEO), zinc oxides (for example Sachtotec), iron oxides or also cerium oxides and/or zirconium oxides.

It may furthermore be preferred for the preparations to comprise inorganic UV filters which have been post-treated by conventional methods, as described, for example, in Cosmetics & Toiletries, 1990, 105, 53-64. One or more of the following post-treatment components can be selected here: amino acids, beeswax, fatty acids, fatty acid alcohols, anionic surfactants, lecithin, phospholipids, sodium, potassium, zinc, iron or aluminium salts of fatty acids, polyethylenes, silicones, proteins (particularly collagen or elastin), alkanolamines, silicon dioxide, aluminium oxide, further metal oxides, phosphates, such as sodium hexametaphosphate, or glycerine.

These inorganic UV filters are generally incorporated into the preparations in an amount of 0.1 percent by weight to 25 percent by weight, preferably 2% by weight-10% by weight.

By combination of one or more of the said compounds having a UV filter action, the protective action against harmful effects of the UV radiation can be optimised.

All said UV filters can also be employed in encapsulated form. In particular, it is advantageous to employ organic UV filters in encapsulated form.

Preferred preparations may also comprise at least one further cosmetic active compound, for example selected from antioxidants, anti-ageing active compounds, anti-wrinkle, anti-flake, anti-acne, deodorants, anti-cellulite active compounds, skin-lightening active compounds or vitamins.

The protective action against oxidative stress or against the effect of free radicals can be improved if the compositions or preparations according to the invention comprise one or more further antioxidants, the person skilled in the art being presented with absolutely no difficulties in selecting antioxidants which act suitably quickly or with a time delay.

There are many proven substances known from the specialist literature which can be used as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, ρ-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to µmol/kg), and also (metal) chelating agents (for example α-hydroxyfatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, ZnSO$_4$), selenium and derivatives thereof (for example selenomethionine), stilbenes and derivatives thereof (for example stilbene oxide, trans-stilbene oxide).

Suitable antioxidants are also compounds of the general formulae A or B

A

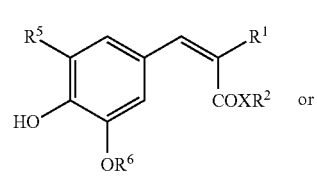

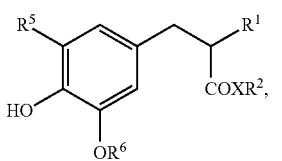

in which
R¹ can be selected from the group —C(O)CH₃, —CO₂R³, —C(O)NH₂ and —C(O)N(R⁴)₂,
X denotes O or NH,
R² denotes linear or branched alkyl having 1 to 30 C atoms,
R³ denotes linear or branched alkyl having 1 to 20 C atoms,
R⁴ in each case, independently of one another, denotes H or linear or branched alkyl having 1 to 8 C atoms,
R⁵ denotes linear or branched alkyl having 1 to 8 C atoms or linear or branched alkoxy having 1 to 8 C atoms, and
R⁶ denotes linear or branched alkyl having 1 to 8 C atoms, preferably derivatives of 2-(4-hydroxy-3,5-dimethoxybenzylidene)malonic acid and/or 2-(4-hydroxy-3,5-dimethoxybenzyl)malonic acid, particularly preferably bis(2-ethylhexyl) 2-(4-hydroxy-3,5-dimethoxybenzylidene)malonate (for example Oxynex® ST Liquid) and/or bis(2-ethylhexyl) 2-(4-hydroxy-3,5-dimethoxybenzyl)malonate (for example RonaCare® AP).

Mixtures of antioxidants are likewise suitable for use in the compositions or preparations according to the invention. Known and commercial mixtures are, for example, mixtures comprising, as active compounds, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed with the compounds of the formula I in such compositions in ratios in the range from 1000:1 to 1:1000, preferably in amounts of 100:1 to 1:100.

Suitable anti-ageing active compounds, in particular for skin-care preparations, are preferably so-called compatible solutes.

The compatible solutes employed are preferably substances selected from the group consisting of pyrimidinecarboxylic acids (such as ectoin and hydroxyectoin), proline, betaine, glutamine, cyclic diphosphoglycerate, N.-acetylornithine, trimethylamine N-oxide di-myo-inositol phosphate (DIP), cyclic 2,3-diphosphoglycerate (cDPG), 1,1-diglycerol phosphate (DGP), β-mannosyl glycerate (firoin), β-mannosyl glyceramide (firoin-A) or/and dimannosyl diinositol phosphate (DMIP) or an optical isomer, derivative, for example an acid, a salt or ester, of these compounds, or combinations thereof.

Additionally, anti-aging active compounds which can be used are products from Merck, such as, for example, 5,7-dihydroxy-2-methylchromone, marketed under the trade name RonaCare®Luremine, or the commercial products RonaCare®Isoquercetin, RonaCare®Tilirosid or RonaCare® Cyclopeptide 5.

The preparations may also comprise one or more further skin-lightening active compounds or synonymously depigmentation active compounds, as described above. Skin-lightening active compounds can in principle be all active compounds known to the person skilled in the art. Examples of compounds having skin-lightening activity have been described above, in particular they are hydroquinone, kojic acid, arbutin, aloesin, niacinamide, azelaic acid, elagic acid, mulberry extract, magnesium ascorbyl phosphate, liquorice extract, emblica, ascorbic acid or rucinol, (E)-3-(4-methoxyphenyl)-acrylic acid (R)-2-((R)-3,4-dihydroxy-5-oxo-2,5-dihydrofuran-2-yl)-2-hydroxyethyl ester or 1-[4-(1,1-dimethylethyl)phenyl]-3-(4-methoxyphenyl)-1,3-propanediol.

The preparations to be employed may comprise vitamins as further ingredients. Preference is given to vitamins and vitamin derivatives selected from vitamin A, vitamin A propionate, vitamin A palmitate, vitamin A acetate, retinol, vitamin B, thiamine chloride hydrochloride (vitamin B₁), riboflavin (vitamin B₂), nicotinamide, vitamin C (ascorbic acid), vitamin D, ergocalciferol (vitamin D₂), vitamin E, DL-α-tocopherol, tocopherol E acetate, tocopherol hydrogensuccinate, vitamin K₁, esculin (vitamin P active compound), thiamine (vitamin B₁), nicotinic acid (niacin), pyridoxine, pyridoxal, pyridoxamine, (vitamin B₆), pantothenic acid, biotin, folic acid and cobalamine (vitamin B₁₂), particularly preferably vitamin A palmitate, vitamin C and derivatives thereof, DL-α-tocopherol, tocopherol E acetate, nicotinic acid, pantothenic acid and biotin. In the case of cosmetic application, vitamins are usually added with the flavonoid-containing premixes or preparations in ranges from 0.01 to 5.0% by weight, based on the total weight.

The retinoids described are at the same time also effective anti-cellulite active compounds. A likewise known anti-cellulite active compound is caffeine.

Furthermore, compounds according to the invention can be combined with all active compounds and assistants as are listed systematically in WO2009/098139. In particular, these substances belong to the use categories stated therein of "Moisturizers and Humectants", "Desquamating agents", "Agents for improving the barrier function", "Depigmenting Agents", "Antioxidants", "Dermo-relaxing or dermo-decontracting agents", "Anti-glycation agents", "Agents for stimulating the synthesis of dermal and/or epidermal macromolecules and/or for preventing their degradation", "Agents for stimulating fibroblast or keratinocyte proliferation and/or keratinocyte differentiation", "Agents for promoting the maturation of the horny envelope", "NO-synthase inhibitors", "Peripheral benzodiazepine receptor (PBR) antagonists", "Agents for increasing the activity of the sebaceous glands", "Agents for stimulating the energy metabolism of cells", "Tensioning agents", "Fat-restructuring agents", "Sliming agents", "Agents for promoting the cutaneous microcirculation", "Calmatives or anti-irritants", "Sebo-regulating or anti-seborrhoic agents", "Astringents", "Cicatrizing agents", "Antiinflammatory agents", "Antiacne agents". The contents of WO 2009/098139 expressly also belong to the disclosure content of the present application.

The said constituents of the preparation can be incorporated in the usual manner, with the aid of techniques which are well known to the person skilled in the art.

Suitable preparations are those for external application, for example can be sprayed onto the skin as cream or milk (O/W, W/O, O/W/O, W/O/W), as lotion or emulsion, in the form of oily-alcoholic, oily-aqueous or aqueousalcoholic gels or solutions. They can be in the form of solid sticks or formulated as an aerosol.

The following may preferably be mentioned as application form of the preparations to be employed: solutions, suspensions, emulsions, PIT emulsions, pastes, ointments, gels, creams, lotions, powders, soaps, surfactant-containing cleansing preparations, oils, aerosols plasters, compresses, bandages and sprays.

Preferred assistants originate from the group of preservatives, stabilisers, solubilisers, colorants, odour improvers.

Ointments, pastes, creams and gels may comprise the customary vehicles which are suitable for topical application, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary readily volatile, liquefied propellants, for example chlorofluorocarbons, propane/butane or dimethyl ether. Compressed air can also advantageously be used.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

A preferred solubiliser in general is 2-isopropyl-5-methylcyclohexanecarbonyl-D-alanine methyl ester.

Suspensions may comprise the customary vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isothionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isothionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glyceryl fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, powder make-up, emulsion make-up and wax make-up, and sunscreen, pre-sun and after-sun preparations.

The preferred preparation forms also include, in particular, emulsions.

Emulsions are advantageous and comprise, for example, the said fats, oils, waxes and other fatty substances, as well as water and an emulsifier, as usually used for a preparation of this type.

The lipid phase may advantageously be selected from the following group of substances:
   mineral oils, mineral waxes
   oils, such as triglycerides of capric or caprylic acid, furthermore natural oils, such as, for example, castor oil;
   fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
   silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of esters of aromatic carboxylic acid and saturated and/or unsaturated, branched and/or unbranched alcohols having a chain length of 3 to 30 C atoms.

The aqueous phase of the preparations to be employed optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol, glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984, 5984, in each case individually or in combination.

The preparation may comprise cosmetic adjuvants which are usually used in this type of preparation, such as, for example, thickeners, softeners, moisturisers, surface-active agents, emulsifiers, preservatives, antifoams, perfumes, waxes, lanolin, propellants, dyes and/or pigments, and other ingredients usually used in cosmetics.

The compounds of the formula I, I-1, IA, IA-1, IB, IB-1, IC or IC-1, as described above or described as preferred, are employed, in particular, in compositions for colouring keratin-containing fibres, in particular for colouring human hair, which are selected, for example, from a coloured setting composition, a coloured blow-dry lotion, a coloured blow-dry foam, a coloured rinse, a coloured gel or a coloured cream. However, they may also be present in compositions for permanent hair colouring, for example in multicomponent systems.

The corresponding compositions for colouring keratin-containing fibres, as described above, preferably comprise the compound(s) of the formula I, I-1, IA, IA-1, IB, IB-1, IC or IC-1, in amounts above 0.01% by weight and below 10% by weight, in each case based on the entire composition. Preferred compositions for colouring keratin-containing fibres are characterised in that they comprise the compound(s) of the formula I, I-1, IA, IA-1, IB, IB-1, IC or IC-1, in amounts of 0.05 to 5% by weight, preferably 0.1 to 2.5% by weight, particularly preferably 0.25 to 1.5% by weight and in particular 0.4 to 1% by weight, in each case based on the entire composition.

The corresponding compositions comprising at least one compound of the formula I, I-1, IA, IA-1, IB, IB-1, IC or IC-1 serve to change the colour of keratin-containing fibres, as described above, in particular human hair. The colour change can take place solely owing to the compound(s) of the formula I, I-1, IA, IA-1, IB, IB-1, IC or IC-1, but the compositions may also additionally comprise further colour-changing substances, for example further direct dyes and/or oxidation colorants. The at least one compound of the formula I, I-1, IA, IA-1, IB, IB-1, IC or IC-1 is preferably used in colorants which additionally comprise 0.001 to 5% by weight of one or more oxidation dye precursors and/or direct dyes.

Oxidation dyes arise through oxidative coupling of one or more development components to one another or to one or more coupler components. Coupler and developer components are also called oxidation dye precursors.

The composition for colouring keratin-containing fibres comprising at least one compound of the formula I, I-1, IA, IA-1, IB, IB-1, IC or IC-1, as described above, can be formulated as a single-component composition, as a two-component composition or as a three-component composition and used correspondingly. Separation in multicomponent systems is appropriate, in particular, where incompatibilities of the ingredients are to be expected or feared. In the case of such systems, the composition to be employed is prepared by the consumer immediately before application by mixing the components.

For example, in the case of permanent hair colouring, a composition comprising the oxidant as first component is often used separately from the further colorant comprising, for example, the oxidation dye precursors.

The invention furthermore relates to a method for colouring keratin-containing fibres, in which a composition for colouring keratin-containing fibres comprising at least one compound of the formula I, I-1, IA, IA-1, IB, IB-1, IC or IC-1, as described above or described as preferred, is applied to the keratin-containing fibre at least once daily or at least twice or a number of times successively, left on the fibre for some time, usually about 20 to 45 minutes, and subsequently rinsed out again or washed out using a shampoo.

The method according to the invention for colouring keratin-containing fibres described in this way is very mild, since it is possible to omit alkalising pre-treatment agents.

However, it is also possible to carry out a pre-treatment of the keratin-containing fibres and then to apply the composition comprising the at least one compound of the formula I, I-1, IA, IA-1, IB, IB-1, IC or IC-1.

A pre-treatment agent of this type may be basic, acidic or neutral, but is preferably basic. The pre-treatment agent preferably comprises $NH_3$ and/or $(NH_4)_2CO_3$. The pre-treatment step is usually carried out before the colouring step, but simultaneous performance of pre-treatment step and colouring step in the case of a corresponding formulation is also conceivable.

The corresponding compositions for colouring comprising at least one compound of the formula I, I-1, IA, IA-1, IB, IB-1, IC or IC-1 are prepared by mixing, in particular dispersing and/or emulsifying and/or dissolving, at least one compound of the formula I, I-1, IA, IA-1, IB, IB-1, IC or IC-1, as described above, with at least one vehicle which is suitable for cosmetic, dermatological preparations and optionally assistants and/or fillers.

Furthermore, in order, for example, to be able to carry out further colour adaptations, the compositions comprising the at least one compound of the formula I, I-1, IA, IA-1, IB, IB-1, IC or IC-1, and/or II may comprise further oxidation dye components.

Coupler components generally allow at least one substitution of a chemical radical of the coupler by the oxidised form of the developer component. A covalent bond forms here between coupler and developer component. Couplers are preferably cyclic compounds which carry at least two groups on the ring, selected from (i) optionally substituted amino groups and/or (ii) hydroxyl groups. These groups are in conjugation through a double-bond system. If the cyclic compound is a six-membered ring, the said groups are preferably located in the ortho-position or meta-position to one another.

Developer components and coupler components are generally employed here in approximately molar amounts to one another. If the molar use has also proven advantageous, a certain excess of individual oxidation dye precursors is not disadvantageous, meaning that developer components and coupler components can be in a molar ratio of 1:0.5 to 1:3, in particular 1:1 to 1:2.

Suitable oxidation dye components of the developer type are p-phenylenediamine and derivatives thereof. Suitable p-phenylenediamines are selected from one or more compounds from the group formed by p-phenylenediamine, p-tolylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis-(2-hydroxyethyl)-p-phenylenediamine, 4-N,N-bis-(2-hydroxyethyl)amino-2-methylaniline, 4-N,N-bis-(2-hydroxyethyl)amino-2-chloroaniline, 2-(2-hydroxyethyl)-p-phenylenediamine, 2-(1,2-dihydroxyethyl)-p-phenylenediamine, 2-fluoro-p-phenylenediamine, 2-isopropyl-p-phenylenediamine, N-(2-hydroxypropyl)-p-phenylenediamine, 2-hydroxymethyl-p-phenylenediamine, N,N-dimethyl-3-methyl-p-phenylenediamine, N-ethyl-N-2-hydroxyethyl-p-phenylenediamine, N-(2,3-dihydroxypropyl)-p-phenylenediamine, N-(4'-aminophenyl)-p-phenylenediamine, N-phenyl-p-phenylenediamine, 2-(2-hydroxyethyloxy)-p-phenylenediamine, 2-methoxymethyl-p-phenylenediamine, 2-(2-acetylaminoethyloxy)-p-phenylenediamine, N-(2-methoxyethyl)-p-phenylenediamine, N-(4-amino-3-methylphenyl)-N-[3-(1H-imidazol-1-yl)propyl]amine, 5,8-diaminobenzo-1,4-dioxane and physiologically tolerated salts thereof. Further suitable p-phenylenediamine derivatives are selected from at least one compound from the group p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, 2-methoxymethyl-p-phenylenediamine and the physiologically tolerated salts of these compounds.

Further suitable developer components which can be employed are compounds which contain at least two aromatic rings which are substituted by amino and/or hydroxyl groups. Further suitable developer components are selected, in particular, from at least one compound from the group formed by N,N'-bis-(2-hydroxyethyl)-N,N'-bis-(4'-aminophenyl)-1,3-diaminopropan-2-ol, N,N'-bis-(2-hydroxyethyl)-N,N'-bis-(4'-aminophenyl)ethylenediamine, N,N'-bis-(4'-aminophenyl)tetramethylenediamine, N,N'-bis-(2-hydroxyethyl)-N,N'-bis-(4'-aminophenyl) tetramethylenediamine, N,N'-bis-(4-(methylamino)phenyl)

tetramethylenediamine, N,N'-diethyl-N,N'-bis-(4'-amino-3'-methylphenyl)ethylenediamine, bis-(2-hydroxy-5-aminophenyl)methane, N,N'-bis-(4'-aminophenyl)-1,4-diazacycloheptane, N,N'-bis-(2-hydroxy-5-aminobenzyl) piperazine, N-(4'-aminophenyl)-p-phenylenediamine and 1,10-bis-(2',5'-diaminophenyl)-1,4,7,10-tetraoxadecane and physiologically tolerated salts thereof. Further suitable bicyclic developer components are selected from N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane or one of the physiologically tolerated salts of these compounds.

It may furthermore be possible to employ a p-aminophenol derivative or one of its physiologically tolerated salts as developer component. Preferred p-aminophenols are p-aminophenol, N-methyl-p-aminophenol, 4-amino-3-methylphenol, 4-amino-3-fluorophenol, 2-hydroxymethyl-amino-4-aminophenol, 4-amino-3-hydroxymethylphenol, 4-amino-2-(2-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(2-hydroxyethylaminomethyl)phenol, 4-amino-2-(1,2-dihydroxyethyl)phenol, 4-amino-2-fluorophenol, 4-amino-2-chlorophenol, 4-amino-2,6-dichlorophenol, 4-amino-2-(diethylaminomethyl)phenol and physiologically tolerated salts thereof. Particularly preferred compounds are p-aminophenol, 4-amino-3-methylphenol, 4-amino-2-aminomethylphenol, 4-amino-2-(1,2-dihydroxyethyl)phenol and 4-amino-2-(diethylaminomethyl)phenol.

Furthermore, the developer component can be selected from o-aminophenol and derivatives thereof, such as, for example, 2-amino-4-methylphenol, 2-amino-5-methylphenol or 2-amino-4-chlorophenol.

Furthermore, the developer component can be selected from heterocyclic developer components, such as, for example, from pyrimidine derivatives, pyrazole derivatives, pyrazolopyrimidine derivatives or physiologically tolerated salts thereof. Preferred pyrimidine derivatives are, in particular, the compounds 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine. Further suitable pyrazole derivatives are the compounds selected from 4,5-diamino-1-methylpyrazole, 4,5-diamino-1-(2-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-t-butyl-1-methylpyrazole, 4,5-diamino-1-t-butyl-3-methylpyrazole, 4,5-diamino-1-(2-hydroxyethyl)-3-methylpyrazole, 4,5-diamino-1-ethyl-3-methylpyrazole, 4,5-diamino-1-ethyl-3-(4-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2-aminoethyl)amino-1,3-dimethylpyrazole, and physiologically tolerated salts thereof, but in particular 4,5-diamino-1-(2-hydroxyethyl)pyrazole. Suitable pyrazolopyrimidines are, in particular, pyrazolo[1,5-a]pyrimidines, where preferred pyrazolo[1,5-a]-pyrimidines are selected from pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo-[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 3-amino-7-dimethylamino-2,5-dimethylpyrazolo[1,5-a]pyrimidine and physiologically tolerated salts thereof and tautomeric forms thereof.

Further suitable developer components are selected from at least one compound from the group formed by p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,M-bis-(2-hydroxyethyl)-N, N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, and the physiologically tolerated salts of these compounds. Further suitable developer components here are p-tolylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole and physiologically tolerated salts thereof.

The developer components are preferably used in an amount of 0.0001 to 10% by weight, preferably 0.001 to 5% by weight, in each case based on the entire colorant.

Suitable oxidation dye components of the coupler type are preferably selected from m-aminophenol and/or derivatives thereof, m-diaminobenzene and/or derivatives thereof, o-diaminobenzene and/or derivatives thereof, o-aminophenol and/or derivatives thereof, naphthalene derivatives containing at least one hydroxyl group, di- or trihydroxybenzene and/or derivatives thereof, pyridine derivatives, pyrimidine derivatives, monohydroxyindole derivatives and/or monoaminoindole derivatives, monohydroxyindoline derivatives and/or monoaminoindoline derivatives, pyrazolone derivatives, such as, for example, 1-phenyl-3-methylpyrazol-5-one, morpholine derivatives, such as, for example, 6-hydroxybenzomorpholine or 6-aminobenzomorpholine, quinoxaline derivatives, such as, for example, 6-methyl-1,2,3,4-tetrahydroquinoxaline, and/or mixtures of two or more compounds from one or more of these classes.

Further coupler components which can be used, such as m-aminophenols or derivatives thereof, are preferably selected from at least one compound from the group formed by 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-diethylaminophenol, N-cyclopentyl-3-aminophenol, 1,3- dihydroxy-5-(methylamitio)benzene, 3-ethylamino-4-methylphenol, 2,4-dichloro-3-aminophenol and physiologically tolerated salts thereof.

Further coupler components which can be used, such as, for example, 3-diaminobenzenes or derivatives thereof, are preferably selected from at least one compound from the group formed by m-phenylenediamine, 2-(2,4-diaminophenoxy)ethanol, 1,3-bis(2,4-diaminophenoxy)propane, 1-methoxy-2-amino-4-(2'-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2'-hydroxyethyl)aminobenzene and physiologically tolerated salts thereof.

Further coupler components which can be used, such as, for example, o-diaminobenzenes or derivatives thereof, are preferably selected from at least one compound from the group formed by 3,4-diaminobenzoic acid and 2,3-diamino-1-methylbenzene and physiologically tolerated salts thereof.

Further coupler components which can be used, such as, for example, di- or trihydroxybenzenes and derivatives thereof, are selected from at least one compound from the group formed by resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene.

Further coupler components which can be used, such as, for example, pyridine derivatives, are selected from at least one compound from the group formed by 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 3,4-diaminopyridine, 2-(2-methoxyethyl)amino-3-amino-6-methoxypyridine, 2-(4'-methoxyphenyl)amino-3-aminopyridine and physiologically tolerated salts thereof.

Naphthalene derivatives containing at least one hydroxyl group which are suitable as coupler component are selected from at least one compound from the group formed by 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-di hydroxynaphthalene.

Indole derivatives which are suitable as coupler component are selected from 4-hydroxyindole, 6-hydroxyindole and 7-hydroxyindole and physiologically tolerated salts thereof.

Indoline derivatives which are suitable as coupler component are preferably selected from 4-hydroxyindoline, 6-hydroxyindoline and 7-hydroxyindoline and physiologically tolerated salts thereof.

Pyrimidine derivatives which are suitable as coupler component are selected from at least one compound from the group formed by 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine and 4,6-dihydroxy-2-methylpyrimidine and physiologically tolerated salts thereof.

Suitable coupler components are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}-amino)ethanol, 2-({3-[(2-hydroxyethylamino]-2-methoxy-5-methylphenyl}-amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or physiologically tolerated salts thereof. Particular preference is given here to resorcinol, 2-methylresorcinol, 5-amino-2-methylphenol, 3-aminophenol, 2-(2,4-diaminophenoxy)ethanol, 1,3-bis-(2,4-diaminophenoxy)propane, 1-methoxy-2-amino-4-(2'-hydroxyethylamino)benzene, 2-amino-3-hydroxypyridine and 1-naphthol and one of the physiologically tolerated salts thereof.

The coupler components are preferably used in an amount of 0.0001 to 10% by weight, preferably 0.001 to 5% by weight, in each case based on the entire composition.

For temporary colourings, use is usually made of colorants or tinting compositions which comprise so-called direct dyes as colouring component. These are dye molecules which are adsorbed directly onto the substrate and do not require an oxidative process for the formation of the colour. These dyes include, for example, henna, which has been known from antiquity for colouring the body and hair. These colourings are generally significantly more sensitive to shampooing than oxidative colourings, with the consequence that a change of shade, which is frequently undesired, or even a visible homogeneous colour loss then occurs very much more quickly.

Furthermore, the compositions according to the invention may comprise at least one further direct dye. These are dyes which are adsorbed directly onto the hair and do not require an oxidative process for the formation of the colour. Direct dyes are usually nitrophenylenediamines, nitroaminophenols, azo dyes, anthraquinones or indophenols.

The direct dyes are in each case preferably employed in an amount of 0.001 to 20% by weight, based on the entire preparation. The total amount of direct dyes is preferably at most 20% by weight.

Preferred anionic direct dyes are the compounds known under the international names (INCI) or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred cationic direct dyes here are
(a) cationic triphenylmethane dyes, such as, for example, Basic Blue 7, Basic Blue 26, Basic Violet 2 and Basic Violet 14, (b) aromatic systems which are substituted by a quaternary nitrogen group, such as, for example, Basic Yellow 57, Basic Red 76, Basic Blue 99, Basic Brown 16 and Basic Brown 17, and (c) direct dyes which contain a heterocycle which contains at least one quaternary nitrogen atom, as mentioned, for example, in claims 6 to 11 of EP-A2-998 908, which is explicitly incorporated herein by way of reference.

Suitable nonionic direct dyes are, in particular, nonionic nitro and quinone dyes and neutral azo dyes.

The direct dyes employed can furthermore also be naturally occurring dyes, as are present, for example, in red henna, neutral henna, black henna, camomile blossom, sandalwood, black tea, alder buckthorn bark, sage, logwood, madder root, catechu, sedre and alkanet root.

The compositions particularly preferably additionally comprise hydrogen peroxide. Compositions of this type for colouring and optionally simultaneously lightening keratin-containing fibres are particularly preferably those which comprise 0.5 to 15% by weight, preferably 1 to 12.5% by weight, particularly preferably 2.5 to 10% by weight and in particular 3 to 6% by weight of hydrogen peroxide (calculated as 100% $H_2O_2$).

The hydrogen peroxide can also be employed in the form of addition compounds thereof onto solid supports, preferably hydrogen peroxide itself is used. The hydrogen peroxide is employed as a solution or in the form of a solid addition compound of hydrogen peroxide onto inorganic or organic compounds, such as, for example, sodium perborate, sodium percarbonate, magnesium percarbonate, sodium percarbamide, polyvinylpyrrolidone $nH_2O_2$ (n is a positive integer greater than 0), urea peroxide and melamine peroxide.

Very particular preference is given to aqueous hydrogen peroxide solutions. The concentration of a hydrogen peroxide solution is determined on the one hand by the legal specifications and on the other hand by the desired effect; 6 to 12 percent solutions in water are preferably used.

For a colour change by means of lightening or bleaching of the substrate, for example the hair, at least one bleach enhancer is preferably additionally employed in cosmetic compositions besides the oxidants.

Bleach enhancers are preferably employed in order to increase the bleaching action of the oxidant, in particular the hydrogen peroxide. Suitable bleach enhancers are (BV-i) compounds which give rise to aliphatic peroxocarboxylic acids and/or optionally substituted perbenzoic acid under perhydrolysis conditions, and/or (BV-ii) carbonate salts and/or hydrogencarbonate salts, and/or (BV-iii) organic carbonates, and/or (BV-iv) carboxylic acids, and/or (BV-v) peroxo compounds.

Bleach enhancers are preferably peroxo compounds, in particular inorganic peroxo compounds. The bleach-enhancing peroxo compounds do not include any addition products of hydrogen peroxide onto other components nor hydrogen peroxide itself. In addition, the choice of peroxo compounds is not subject to any restrictions. Preferred peroxo compounds are peroxydisulfate salts, persulfate salts, peroxydiphosphate salts (in particular ammonium peroxydisulfate, potassium peroxydisulfate, sodium peroxydisulfate, ammonium persulfate, potassium persulfate, sodium persulfate, potassium peroxydiphosphate) and peroxides (such as barium peroxide and magnesium peroxide). Of these peroxo compounds, which can also be employed in combination, preference is given in accordance with the invention to the peroxydisulfates, in particular ammonium peroxydisulfate. Preference is given here to compositions for colouring and optionally simultaneously lightening keratinic fibres which additionally comprise 0.01 to 2% by weight of at least one solid peroxo compound, which is selected from ammonium, alkali-metal and alkaline-earth metal persulfates, peroxomonosulfates and peroxydisulfates, where preferred compositions comprise peroxydisulfates, which are preferably selected from sodium peroxydisulfate and/or potassium peroxydisulfate and/or ammonium peroxydisulfate, and where preferred compositions comprise at least two different peroxydisulfates.

Particular preference is furthermore given to persulfates, in particular the mixture of potassium peroxosulfate, potassium hydrogensulfate and potassium sulfate known as Caro's salt.

The bleach enhancers are preferably present in the cosmetic compositions according to the invention in amounts of 5 to 30% by weight, in particular in amounts of 8 to 20% by weight, in each case based on the weight of the ready-to-use composition.

Furthermore, it has proven advantageous for the colorants and/or lightening compositions to comprise non-ionogenic surface-active substances.

Preference is given here to surface-active substances which have an HLB value of 5.0 or greater. For the definition of the HLB value, reference is expressly made to the comments in Hugo Janistyn, Handbuch der Kosmetika and Riechstoffe [Handbook of Cosmetics and Fragrances], Volume III: Die Körperpflegemittel [Body-Care Compositions], 2nd Edition, Dr Alfred Hüthig Verlag Heidelberg, 1973, pages 68-78 and Hugo Janistyn, Taschenbuch der modernen Parfümerie and Kosmetik [Pocketbook of Modern Perfumery and Cosmetics], 4th Edition, Wissenschaftliche Verlagsgesellschaft m.b.H. Stuttgart, 1974, pages 466-474, and the original papers cited therein.

Owing to the simple processability, particularly preferred non-ionogenic surface-active substances here are substances which are commercially available in pure form as solids or liquids. The definition of purity in this connection does not relate to chemically pure compounds. Instead, in particular in the case of natural products, it is possible to employ mixtures of different homologues, for example having different alkyl chain lengths, as are obtained in the case of products based on natural fats and oils. Also in the case of alkoxylated products, mixtures of different degrees of alkoxylation are usually present. The term purity in this connection instead relates to the fact that the substances selected should preferably be free from solvents, extenders and other accompanying substances.

As further constituent, the compositions according to the invention may comprise at least one ammonium compound from the group ammonium chloride, ammonium carbonate, ammonium bicarbonate, ammonium sulfate and/or ammonium carbamate in an amount of 0.5 to 10, preferably 1 to 5% by weight, based on the entire composition.

Furthermore, the colorants and/or lightening compositions according to the invention may comprise further active compounds, assistants and additives, such as, for example, nonionic polymers, such as, for example, vinylpyrrolidone-vinyl acrylate copolymers, poyvinylpyrrolidone and vinylpyrrolidone-vinyl acetate copolymers and polysiloxanes, cationic polymers, such as quaternised cellulose ethers, polysiloxanes containing quaternary groups, dimethyldiallylammonium chloride polymers, acrylamide-dimethyldiallylammonium chloride copolymers, diethyl sulfate-quaternised dimethylaminoethyl methacrylate-vinylpyrrolidone copolymers, vinylpyrrolidone-imidazolinium methochloride copolymers and quaternised polyvinyl alcohol, zwitterionic and amphoteric polymers, such as, for example, acrylamidopropyltrimethylammonium chloride-acrylate copolymers and octylacrylamide-methyl methacrylate-tert-butylaminoethyl methacrylate-2-hydroxypropyl methacrylate copolymers, anionic polymers, such as, for example, polyacrylic acids, crosslinked polyacrylic acids, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and acrylic acid-ethyl acrylate-N-tert-butylacrylamide terpolymers, thickeners, such as agar-agar, guar gum, alginates, xanthan gum, gum arabic, karaya gum, carob seed flour, linseed gums, dextrans, cellulose derivatives, for example methylcellulose, hydroxyalkylcellulose and carboxymethylcellulose, starch fractions and derivatives, such as amylose, amylopectin and dextrins, clays, such as, for example, bentonite or fully synthetic hydrocolloids, such as, for example, polyvinyl alcohol, structurants, such as maleic acid and lactic acid, hair-conditioning compounds, such as phospholipids, for example soya lecithin, egg lecitin and cephalins, protein hydrolysates, in particular elastin, collagen, keratin, milk protein, soya protein and wheat protein hydrolysates, condensation products thereof with fatty acids and quaternised protein hydrolysates, perfume oils, dimethylisosorbide and cyclodextrins, solvents and solubilisers, such as ethanol, isopropanol, ethylene glycol, propylene glycol, propylene glycol, glycerol and diethylene glycol, fibre structure-improving active compounds, in particular mono-, di- and oligosaccharides, such as, for example, glucose, galactose, fructose, fruit sugar and lactose, quaternised amines, such as methyl-1-alkylamidoethyl-2-alkylimidazolinium methosulfate antifoams, such as silicones, dyes for tinting the composition, antidandruff active compounds, such as Piroctone Olamine, Zink Omadine and climbazole, light-protection agents, in particular derivatised benzophenones, cinnamic acid derivatives and triazines, substances for adjusting the pH, such as, for example, conventional acids, in particular edible acids and bases, active compounds, such as panthenol, pantothenic acid, allantoin, pyrrolidonecarboxylic acids and salts thereof, as well as bisabolol, vitamins, provitamins and vitamin precursors, in particular those from groups A, $B_3$, $B_5$, $B_6$, C, E, F and H, plant extracts, such as the extracts from green tea, oak bark, stinging nettles, witch hazel, hops, camomile, burdock root, horsetail, hawthorn, linden blossom, almonds, aloe vera, spruce needles, horse chestnut, sandalwood, juniper, coconut, mango, apricot, lime, wheat, kiwi, melon, orange, grapefruit, sage, rosemary, birch, mallow, cuckoo flower, wild thyme, yarrow, thyme, lemon balm, restharrow, coltsfoot, marshmallow, meristem, ginseng and ginger root, cholesterol, consistency modifiers, such as sugar esters, polyol esters or polyalkyl ethers, fats and waxes, such as spermaceti, beeswax, montan wax and paraffins, fatty alcohols and fatty acid esters, fatty acid alkanolamides, complexing agents, such as EDTA, NTA, β-alaninediacetic acid and phosphonic acids, swelling and penetration substances, such as glycerol, propylene glycol monoethyl ether, carbonates, hydrogencarbonates, guanidines, ureas and primary, secondary and tertiary phosphates, opacifiers, such as latex, styrene-PVP and styrene-acrylamide copolymers pearlescent agents, such as ethylene glycol mono- and distearate and PEG-3 distearate, pigments, stabilisers for hydrogen peroxide and other oxidants, blowing agents, such as propane/butane mixtures, $N_2O$, dimethyl ether, $CO_2$ and air, antioxidants.

With respect to further optional components and the amounts of these components employed, express reference is made to the relevant handbooks known to the person skilled in the art, for example Kh. Schrader, Grundlagen and Rezepturen der Kosmetika [Principles and Recipes of Cosmetics], 2nd Edition, Hüthig Buch Verlag, Heidelberg, 1989.

The compositions according to the invention for colouring keratin-containing fibres can contain the ingredients in a suitable aqueous, alcoholic or aqueous/alcoholic vehicle. For the purposes of hair colouring, vehicles of this type are, for example, creams, emulsions, gels or also surfactant-containing foaming solutions, such as, for example, shampoos, foam aerosols or other preparations which are suitable for application to the hair. However, it is also possible to prepare a pulverulent or also tablet-form formulation, which is preferred for colorants and/or lightening compositions.

Aqueous/alcoholic solutions are taken to mean, for example, aqueous solutions comprising 3 to 70% by weight of a $C_1$-$C_4$ alcohol, in particular ethanol or isopropanol. Aqueous/alcoholic solutions of this type may additionally comprise further organic solvents, such as, for example, methoxybutanol, benzyl alcohol, ethyl diglycol or 1,2-propylene glycol. Preference is given here to all water-soluble organic solvents.

Preferred compositions are characterised in that they additionally comprise a non-aqueous solvent, where particularly preferred compositions comprise the solvent in a concentration of 0.1-30 percent by weight, preferably in a concentration of 1-20 percent by weight, very particularly preferably in a concentration of 2-10 percent by weight, in each case based on the composition.

In further preferred compositions, the solvent is selected from ethanol, n-propanol, isopropanol, n-butanol, propylene glycol, n-butylene glycol, glycerol, diethylene glycol monoethyl ether, diethylene glycol mono-n-butyl ether, phenoxyethanol and benzyl alcohol and mixtures thereof.

The pH of the compositions according to the invention can be adjusted in a broad range through suitable ingredients, such as acidifying agents or alkalising agents.

Oxidative colouring of keratin-containing fibres can in principle be carried out with atmospheric oxygen in the presence of oxidation dye precursors. However, preference is given to the use of a chemical oxidant. Suitable oxidants are persulfates, chlorites and in particular hydrogen peroxide or addition products thereof, as described above.

In addition, the compositions may comprise metal ions or metal ion complexes, for example Cu, Fe, Mn or Ru ions or complexes of these ions. Furthermore, the presence of complexing agents is advantageous in the case of addition of these metal ions. The complexing agents here can be selected from polycarboxylic acids, geminal diphosphonic acids, aminophosphonic acids, phosphonopolycarboxylic acids, cyclodextrins, aminodicarboxylic acids, polyacetals or phosphonates.

The compositions are preferably formulated to be low-water or water-free. Preferred compositions are characterised in that they comprise less than 5% by weight, preferably less than 2% by weight, particularly preferably less than 1% by weight and in particular less than 0.5% by weight of water. The water content of the compositions can be determined, for example, by means of Karl Fischer titration.

Even without further comments, it is assumed that a person skilled in the art will be able to utilise the above description in the broadest scope. The preferred embodiments and examples should therefore merely be regarded as descriptive disclosure which is absolutely not limiting in any way. The complete disclosure content of all applications and publications mentioned above and below is incorporated into this application by way of reference. The percent by weight ratios of the individual ingredients in the preparations of the examples expressly belong to the disclosure content of the description and can therefore be utilised as features.

Further important features and advantages of the invention arise from the sub-claims and from the examples.

It goes without saying that the features mentioned above and still to be explained below can be used not only in the respective combination indicated, but also in other combinations or in isolation without leaving the framework of the present invention.

Preferred embodiments of the invention are described in the examples and are explained in greater detail in the following description without restricting the scope of the present invention.

EXAMPLE 1

2,2-Dimethyl-5-oxohexahydrofuro[2',3':4,5]-furo[2,3-d]-1,3-dioxol-6-yl(E)-3-phenylacrylate

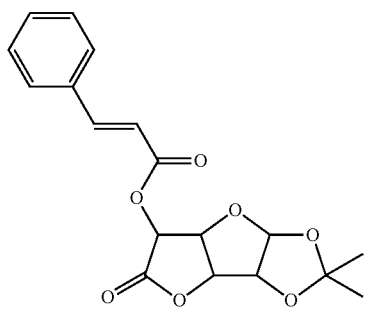 [SMILES: CC1(C)OC2OC3C(OC(=O)/C=C/c4ccccc4)C(=O)OC3C2O1]

385 μl (2.78 mmol) of triethylamine are slowly added dropwise to a solution of 500 mg (2.31 mmol) of D-glucurono-6,3-acetonide and 462 mg (2.78 mmol) of cinnamoyl chloride in 12 ml of dichloromethane. A rise in temperature by 5° C. is observed. Stirring is continued at room temperature for 16 h. For work-up, 10 ml of 1N HCl are added, and the phases are then separated. The organic phase is washed again with water, dried over sodium sulfate, filtered and evaporated in a rotary evaporator in vacuo, giving 810 mg of yellowish oil.

$^1$H-NMR (400 MHz, DMSO-$d_6$): δ=1.27 (s, 3H), 1.41 (s, 3H), 4.88 (d, 1H, J=3.7 Hz), 5.06 (m, 2H), 5.96 (d, 1H, J=3.8 Hz), 6.03 (d, 1H, J=3.7 Hz), 6.73 (d, 1H, J=16 Hz), 7.42 (m, 3H), 7.73 (m, 2H), 7.77 (d, 1H, J=16.2 Hz).

EXAMPLE 2

2,2-Dimethyl-5-oxohexahydrofuro[2',3':4,5]furo[2,3-d]-1,3-dioxol-6-yl(E)-3-(4-methoxyphenyl)acrylate

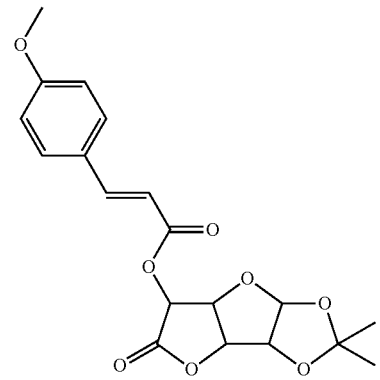 [SMILES: COc1ccc(/C=C/C(=O)OC2C(=O)OC3C4OC(C)(C)OC4OC23)cc1]

5.80 ml (2.78 mmol) of triethylamine are slowly added dropwise at room temperature to a solution of 7.50 g (34.7 mmol) of D-glucurono-6,3-acetonide and 8.10 g (41.2 mmol) of E-4-methoxycinnamoyl chloride in 150 ml of dichloromethane. A rise in temperature by 10° C. is observed. Stirring is continued at room temperature for 16 h. For work-up, 100 ml of 1N HCl are added, and the phases are then separated. The organic phase is washed again with water and then with sat. sodium chloride solution, dried over sodium sulfate, filtered and evaporated in a rotary evaporator in vacuo. The crude product is separated on silica gel (300 g, heptane/ethyl acetate 2:1), and the fraction at $R_f$=0.55 is collected. Removal of the solvents by distillation gives 7.7 g of product (59% of theory) as pale-yellow foam.

$^1$H-NMR (400 MHz, DMSO-$d_6$): δ=1.30 (s, 3H), 1.45 (s, 3H), 3.82 (s, 3H), 4.92 (d, 1H, J=3.9 Hz), 5.06 (m, 2H), 5.99 (d, 1H, J=3.9 Hz), 6.06 (d, 1H, J=3.7 Hz), 6.63 (d, 1H, J=16 Hz), 7.00 (m, 2H), 7.74 (m, 3H).

EXAMPLE 3

2,2-Dimethyl-5-oxohexahydrofuro[2',3':4,5]furo[2,3-d]-1,3-dioxol-6-yl acetate

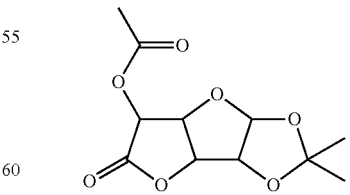

With exclusion of oxygen, 10.0 g (46.3 mmol) of D-lucorono-6,3-acetonide are dissolved in 40 ml of acetic anhydride under anhydrous conditions. A spatula tip of iodine is then added. The temperature of the red solution rises to 24° C., and the reaction mixture becomes a brown colour.

Stirring is continued at room temperature for 16 h. The excess iodine is removed using sodium thiosulfate solution with ice-cooling. 25 ml of water are added, and the mixture is stirred for a further 1 h. The mixture is extracted with dichloromethane, and the phases are separated. The aqueous phase is extracted again with dichloromethane, and the combined organic phases are washed with NaHCO$_3$ solution and then with sat. sodium chloride solution until neutral. The mixture is dried over sodium sulfate, filtered and evaporated in a rotary evaporator in vacuo, giving 14.6 g of crude product, which are purified on silica gel (420 g, heptane/ethyl acetate 1:2). Active carbon is added to the combined product fractions having an $R_f$=0.5, and the mixture is subsequently filtered. Removal of the solvent by distillation gives 9.0 g (76% of theory) of yellow oil as diastereomer mixture.

$^1$H-NMR (400 MHz, DMSO-d$_6$): δ=1.38 (s, 3H), 1.43 (s, 3H), 1.45 (s, 3H), 1.47 (s, 3H), 2.05 (s, 3H), 2.13 (s, 3H), 4.50 (dd, 1H, J=8.0 Hz, J=2.6 Hz), 4.54 (dd, 1H, J=8.0 Hz, J=3.7 Hz), 4.90 (dd, 1H, J=8.1 Hz, J=3.1 Hz), 5.06 (dd, 1H, J=8.0 Hz, J=3.7 Hz), 5.61 (dd, 1H, J=5.5 Hz, J=3.7 Hz), 5.88 (dd, 1H, J=5.2 Hz, J=3.1 Hz), 5.99 (d, 1H, J=5.2 Hz), 6.10 (d, 1H, J=5.5 Hz), 6.26 (d, 1H, J=3.7 Hz), 6.30 (d, 1H, J=2.6 Hz).

USE EXAMPLES

Example A

Liquid Skin Model 1 mmol of the respective glucuronolactone derivative, as indicated in the following table, and 1 mmol (146 mg) of L-lysine are weighed out into a 100 ml volumetric flask. The mixture is subsequently made up to the mark with a mixture of 6 ml of phosphate-buffered water (pH=7) and 94 ml of ethylene glycol. The reaction is observed with vigorous stirring, and the L*a*b* values are determined after 24 hours.
Results after 24 Hours:

| Compounds | L* | a* | b* |
| --- | --- | --- | --- |
| Compound (Ia) | 66.34 | 34.88 | 105.16 |
| Compound (Ig) | 64.09 | 36.87 | 103.8 |
| Compound I(o) | 87.51 | 2.41 | 92.10 |
| Glucuronolactone | 94.30 | −6.94 | 38.68 |
| DHA | 34.95 | 24.91 | 57.45 |
| Erythrulose | 93.50 | −4.40 | 32.66 |

After 24 hours, compounds (Ia), (Ig), (Io) exhibit lower L values than erythrulose or glucuronolactone. Glucuronolactone exhibits a comparable colour effect to erythrulose at an identical concentration in the test formulation.

The results confirm that the compounds according to the invention produce a darker colour in the selected test system compared with erythrulose or glucuronolactone. The a values of the compounds according to the invention are higher than the a values of DHA and/or erythrulose. The compounds of the formula I are therefore capable of achieving a hue which is shifted more towards red, in particular the compounds of the formula (Ia) and (Ig).

Example B

Colouring Test

In each case, 1 mmol of the substance to be tested are weighed out into a 100 ml conical flask with ground-glass joint:

(1) DHA: 90 mg
(2) Glucuronolactone: 176 mg
(3) Compound (Ia): 376 mg
(4) Compound (Ig): 320 mg
(5) Compound (Io): 258 mg A merino wool ball with the size of a grape and a magnetic stirrer are then added to each conical flask.

A mixture of 6% by vol. of buffer (ph7) and 94% by vol. of ethylene glycol is then prepared, 100 ml of this mixture are added to each conical flask and stirred at RT for 24 h.

After 24 h, the wool balls are washed firstly with water, then with warm washing-powder solution and again with water and dried.

The wool samples which have been treated with DHA exhibit no coloration compared with the untreated sample. Glucuronolactone exhibits a very pale-yellow coloration. The wool samples which have been treated with compound (Io) likewise exhibit a pale-yellow coloration. Compared with the colouring result with glucuronolactone, the yellow coloration is stronger. The wool samples which have been treated with compound (Ig) exhibit a yellow coloration. The wool samples which have been treated with compound (Ia) exhibit an orange-yellow coloration.

This colouring result can also be applied to hair, since merino wool, like hair, is built up from proteins (keratins) and the outermost layer is in each case the cuticle.

Example C

Ex-Vivo Study 24 histological explants having an average diameter of 10 mm are prepared from the lower abdomen tissue of a 36-year-old European woman. The pieces of tissue are kept in BEM medium (BIO-EC's Explants Medium) at 37° C. in a humid atmosphere comprising 5% of CO$_2$.

The tissue is divided into 8 batches of 3 explants each:
A negative control (untreated sample, treated only with the vehicle Mygliol)→E
A positive control (4% dihydroxyacetone)→R1
A positive control (4% erythrulose)→R2
Glucuronolactone (4%)→P1
Compound of the formula (Ig) (4%)→P2
Compound of the formula (Ia) (4%)→P3

30 μl of the substance solutions are applied on 10 consecutive days using a round filter paper and left to act for 2 h. On days 1, 3 and 7, the explants are measured chromametrically.

The colour measurements are carried out using a Minolta CR-300 Chroma-meter, and the L, a and b values are read off correspondingly on the instrument.
Principle of the Chromametric Measurement:
The following parameters are set:
In 1931, a test series was carried out by the CIE (Commision Internationale de L'Eclairage), where the "2-degree standard observer" was defined. A colour area is present here which is viewed at a viewing angle of 2 degrees. This viewing angle is used as standard in the chromametric measurement.
Irradiation source D65, corresponding to daylight
Region of the measurement: 3 mm
Parameters used: L*a*b*
The sample is placed on the bearing rail with the epidermis facing downwards. The irradiation is carried out from the underside through the area indicated (3 mm).

Contrast Study:

In the colorimetric determinations <<L a b>>, the L value determines the contrast of the skin. If the L value drops, the skin appears darker.

ITA is defined as arctang[(L-50)/b]. If the ITA index increases, the skin appears paler.

Results:

|      | Day 1 (ITA value) | Day 3 (ITA value) | Day 7 (ITA value) |
|------|-------------------|-------------------|-------------------|
| (E)  | +5%               | 0%                | −1%               |
| (R1) | −3%               | 0%                | −1%               |

|      | Day 1 (ITA value) | Day 3 (ITA value) | Day 7 (ITA value) |
|------|-------------------|-------------------|-------------------|
| (R2) | 4%                | −4%               | 4%                |
| (P1) | 10%               | 4%                | −2%               |
| (P2) | −2%               | 1%                | −2%               |
| (P3) | −6%               | −5%               | −10%              |

Formulation Example 1

O/W Tanning Cream

| Constituents/trade name | Source of supply | INCI | [% by wt.] |
|---|---|---|---|
| A | | | |
| Tego Care 150 | (1) | GLYCERYL STEARATE, STEARETH-25-CETETH-20, STEARYL ALCOHOL | 8 |
| Miglyol 812 N | (2) | CAPRYLIC/CAPRIC TRIGLYCERIDE | 3 |
| Isopropyl myristate | (3) | ISOPROPYL MYRISTATE | 2 |
| Paraffin liquid | (4) | PARAFFINUM LIQUIDUM (MINERAL OIL) | 12 |
| Paraffin | (4) | PARAFFIN | 2 |
| Propyl 4-hydroxybenzoate | (4) | PROPYLPARABEN | 0.15 |
| Compound (Ia) | | | 4 |
| B | | | |
| 1,2-Propanediol | (4) | PROPYLENE GLYCOL | 4 |
| Sorbitol F liquid | (4) | SORBITOL | 2 |
| Methyl 4-hydroxybenzoate | (4) | METHYLPARABEN | 0.05 |
| Water, demineralised | | AQUA (WATER) | to 100 |
| C | | | |
| Water, demineralised | | | 11.8 |
| D | | | |
| Perfume (q.s.) | | PARFUM | 0.50 |
| Total | | | 100.00 |

Preparation Process:

Firstly, phases A and B are warmed separately to 75° C. Phase A is then slowly added to phase B with careful stirring. The mixture is homogenised at 65° C. for one minute. The mixture is subsequently cooled to 40° C. with stirring, and phase C is added with stirring, the mixture is cooled to 35° C., and phase D is added, and cooling is continued.

Sources of Supply:

(1) Degussa-Goldschmidt AG (2) Sasol Germany GmbH (3) Cognis GmbH (4) Merck KGaAJRona®

Formulation Example 2

O/W Tanning Cream

| Constituents/trade name | Source of supply | INCI | [% by wt.] |
|---|---|---|---|
| A | | | |
| Tego Care 150 | (1) | GLYCERYL STEARATE, STEARETH-25, CETETH-20, STEARYL ALCOHOL | 8 |
| Lanette O | (2) | CETEARYL ALCOHOL | 1.5 |
| Luvitol EHO | (3) | CETEARYL OCTANOATE | 5 |

| Constituents/trade name | Source of supply | INCI | [% by wt.] |
|---|---|---|---|
| Miglyol 812 N | (4) | CAPRYLIC/CAPRIC TRIGLYCERIDE | 5 |
| Paraffin liquid | (5) | PARAFFINUM LIQUIDUM (MINERAL OIL) | 3 |
| AbilWax 2434 | (1) | STEAROXY DIMETHICONE | 1.6 |
| Dow Corning 200 Fluid (350 cs) | (6) | DIMETHICONE | 0.5 |
| Propyl 4-hydroxybenzoate | (5) | PROPYLLPARABEN | 0.05 |
| B | | | |
| 1,2-Propanediol | (5) | PROPYLENE GLYCOL | 3 |
| Methyl 4-hydroxybenzoate | (5) | METHYLPARABEN | 0.15 |
| Water, demineralized | | AQUA (WATER) | to 100 |
| C | | | |
| Dihydroxyacetone | (8) | DIHYDROXYACETONE | 5 |
| Probiol L 05018 (Empty liposomes) | (7) | AQUA, ALCOHOL DENAT, LECITHIN, GLYCERINE, DISODIUM PHOSPHATE | 5 |
| Water, demineralized | | AQUA (WATER) | 10.00 |
| Compound (Ia) | (9) | | 1 |
| Total | | | 100.00 |

Preparation Process:

Firstly, phases A and B are warmed to 80° C. Phase B is then slowly added to phase A with stirring and homogenised. The mixture is then cooled, and phase C is added at 40° C.

Sources of Supply:

(1) Degussa-Goldschmidt AG, (2) Cognis GmbH, (3) BASF AG, (4) Sasol Germany GmbH, (5) Merck KGaA/Rona®, (6) Dow Corning (7) Kuhs GmbH & Co. KG, (8) Merck KGaA/Rona®, (9) Alfa Aesar Formulation Example 3

O/W Tanning Lotion

| Constituents/trade name | Source of supply | INCI | [% by wt.] |
|---|---|---|---|
| A | | | |
| Montanov 68 | (1) | CETEARYL ALCOHOL, CETEARYL GLUCOSIDE | 4 |
| Span 60 | (2) | SORBITAN STEARATE | 1.5 |
| Lanette O | (3) | CETEARYL ALCOHOL | 1 |
| Cosmacol ELI | (4) | C12-13 ALIKYL LACTATE | 2 |
| Arimol HD | (2) | ISOHEXADECANE | 1 |
| Paraffin highly liquid | (5) | PARAFFINUM LIQUIDUM (MINERAL OIL) | 3 |
| Dow Corning 9050 Silicone Elastomer Blend | (6) | CYCLOMETHICONE, DIMETHICONE CROSSPOLYMER | 2 |
| RonaCare ® Tocopherol Acetate | (5) | TOCOPHERYL ACETATE | 0.5 |
| Propyl 4-hydroxybenzoate | (5) | PROPYLPARABEN | 0.05 |
| B | | | |
| RonaCare ® Ectoin | (5) | ECTOIN | 0.5 |
| Glycerol, anhydrous | (5) | GLYCERINE | 2 |
| Water, demineralized | | AQUA (WATER) | to 100 |
| Methyl 4-hydroxybenzoate | (5) | METHYLPARABEN | 0.15 |
| C | | | |
| Rhodicare S | (7) | XANTHAN GUM | 0.2 |
| D | | | |
| Probiol L 05018 (Empty liposomes) | (8) | AQUA, ALCOHOL DENAT, LECITHIN, GLYCERINE, DISODIUM PHOSPHATE | 5 |

-continued

| Constituents/trade name | Source of supply | INCI | [% by wt.] |
|---|---|---|---|
| Compound (Ig) | | | 4 |
| Water, demineralised | | AQUA (WATER) | 10 |
| E | | | |
| Fragrance Cucumber | (9) | PARFUM | 0.2 |
| Total | | | 100.00 |

Preparation Process:

Firstly, phases A and B are mixed separately and warmed to 75° C. Phase C is then added to phase B and added to phase A with stirring. The mixture is homogenised. The mixture is then cooled with stirring, and phases D and E are added at 40° C.

Sources of Supply:
(1) Seppic (2) Uniqema (3) Cognis GmbH
(4) Condea Chinica D.A.C.S.p.A. (5) Merck KGaA/Rona®
(6) Dow Corning (7) Rhodia GmbH (8) Kuhs GmbH & Co. KG (9) Drom Formulation Example 4

Mild Transparent W/O Tanning Lotion

| Constituents/trade name | Source of supply | INCI | [% by wt.] |
|---|---|---|---|
| A | | | |
| Dow Corning 3225 C | (1) | CYCLOMETHICONE, DIMETHICONE COPOLYOL | 23.6 |
| Propyl 4-hydroxybenzoate | (2) | PROPYLPARABEN | 0.05 |
| B | | | |
| Dihydroxyacetone | (3) | DIHYDROXYACETONE | 3 |
| Compound (Io) | (4) | | 2 |
| Methyl 4-hydroxybenzoate | (2) | METHYLPARABEN | 0.15 |
| 1,2-Propanediol | (2) | PROPYLENE GLYCOL | 35.9 |
| Water, demineralized | | AQUA (WATER) | to 100 |
| Total | | | 100.00 |

Preparation Process:
Firstly, phase B is dissolved and then added to phase A. The pH is adjusted to the value pH=6.0 using sodium hydroxide solution or citric acid.

Sources of Supply:
(1) Dow Corning (2) Merck KGaA/Rona® (3) Merck KGaA/Rona® (4) Alfa Aesar Formulation Example 5

O/W Tanning Cream with UV A/B Protection

| Constituents/trade name | Source of supply | INCI | [% by wt.] |
|---|---|---|---|
| A | | | |
| Eusolex ® 2292 | (1) | ETHYLHEXYL METHOXYCINNAMATE, BHT | 3 |
| Eusolex ® 4360 | (1) | BENZOPHENONE-3 | 0.5 |
| Tego Care 150 | (2) | GLYCERYL STEARATE, STEARETH-25, CETETH-20, STEARYL ALCOHOL | 8 |
| Lanette O | (3) | CETEARYL ALCOHOL | 1.5 |
| Luvitol EHO | (4) | CETEARYL OCTANOATE | 5 |
| Miglyoll 812 N | (5) | CAPRYLIC/CAPRIC TRIGLYCERIDE | 5 |

-continued

| Constituents/trade name | Source of supply | INCI | [% by wt.] |
|---|---|---|---|
| Paraffin liquid | (1) | PARAFFINUM LIQUIDUM (MINERAL OIL) | 3 |
| Abil-Wax 2434 | (2) | STEAROXY DIMETHICONE | 1.6 |
| Dow Corning 200 Fluid (350 cs) | (6) | DIMETHICONE | 0.5 |
| Propyl 4-hydroxybenzoate | (1) | PROPYLPARABEN | 0.05 |
| B | | | |
| 1,2-Propanediol | (1) | PROPYLENE GLYCOL | 3 |
| Methyl 4-hydroxybenzoate sodium salt | (1) | SODIUM METHYLPARABEN | 0.17 |
| Water, demineralised | | AQUA (WATER) | to 100 |
| Compound (Io) | | | 5 |
| C | | | |
| Dihydroxyacetone | (7) | DIHYDROXYACETONE | 5 |
| Water, demineralised | | | 10 |
| Total | | | 100.00 |

Preparation Process:

Firstly, phases A and B are mixed separately and warmed to 80° C. Phase B is then slowly added to phase A with stirring. The mixture is homogenised and cooled to 40° C., and phase C is added, then cooled to room temperature.

Sources of Supply:
(1) Merck KGaA/Rona® (2) Degussa-Goldschmidt AG (3) Cognis GmbH (4) BASF AG (5) Sasol Germany GmbH (6) Dow Corning (7) Merck KGaA/Rona®

Formulation Example 6

O/W Shimmering Tanning Lotion

| Constituents/trade name | Source of supply | INCI | [% by wt.] |
|---|---|---|---|
| A | | | |
| Montanov 68 | (1) | CETEARYL ALCOHOL, CETEARYL GLUCOSIDE | 4 |
| Span 60 | (2) | SORBITAN STEARATE | 1.5 |
| Lanette O | (3) | CETEARYL ALCOHOL | 1 |
| Cosmacol ELI | (4) | C12-13 ALKYL LACTATE | 3 |
| Cosmacol EMI | (4) | DI-C12-13 ALKYL MALATE | 1 |
| Dow Corning 9040 Silicone Elastomer Blend | (5) | CYCLOMETHICONE, DIMETHICONE CROSSPOLYMER | 1 |
| Arlamol HD | (2) | ISOHEXADECANE | 3 |
| RonaCare ® Tocopherol Acetate | (6) | TOCOPHERYL ACETATE | 0.5 |
| Propyl 4-hydroxybenzoate | (6) | PROPYLPARABEN | 0.05 |
| B | | | |
| RonaCare ® Ectoin | (6) | ECTOIN | 0.5 |
| Colorona ® Red Gold | (6) | MICA, CI 77891 (TITANIUM DIOXIDE), CI 77491 (ION OXIDES) | 2 |
| Glycerol, anhydrous | (6) | GLYCERIN | 2 |
| Caramel 250 | (7) | CARAMEL | 1 |
| FD&C Yellow No6 W082 | (8) | CI 15985 | 0.01 |
| Water, demineralized | | AQUA (WATER) | to 100 |
| Methyl 4-hydroxybenzoate | (6) | METHYLPARABEN | 0.15 |
| Compound Ia | (11) | | 1 |
| C | | | |
| Sepigel 305 | (1) | LAURETH-7, POLYACRYLAMIDE, C13-14 ISOPARAFFIN | 0.5 |
| D | | | |
| Dihydroxyacetone | (10) | DIHYDROXYACETONE | 5 |
| Water, demineralised | | | 10 |

-continued

| Constituents/trade name | Source of supply | INCI | [% by wt.] |
|---|---|---|---|
| E | | | |
| Fragrance Babylon | (9) | PARFUM | 0.2 |
| Total | | | 100.00 |

Preparation Process:

Firstly, phases A and B are warmed separately to 75° C. Phase A is then slowly added to phase B with stirring. Phase C is added to A/B at 60° C., and the mixture is homogenised. The mixture is subsequently cooled to 40° C., and phases D and E are added successively.

Sources of Supply:
(1) Seppic (2) Uniqema (3) Cognis GmbH
(4) Condea Chimica D.A.C.S.p.A. (5) Dow Corning (6) Merck KGaA/Rona®
(7) D. D. Williamson (8) Les Colorants Wackherr SA (9) Drom (10) Merck KGaA/Rona® (11) Alfa Aesar

The invention claimed is:

1. A method for tanning skin, comprising tanning said skin by administering these to an effective amount of at least one compound of the formula I

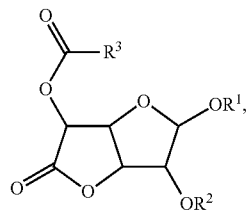

where
$R^1$ and $R^2$ each, independently of one another, denote
a straight-chain or branched alkyl group having 1 to 30 C atoms,
and
either $R^1$ or $R^2$ may denote H,
or
$R^1$ and $R^2$ together form an unsubstituted or substituted five-membered ring, which may be substituted
a) by at least one straight-chain or branched alkyl group having 1 to 30 C atoms and/or
b) by at least one aryl group having 6 to 12 C atoms,
where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl,
$R^3$ denotes a straight-chain or branched alkyl group having 1 to 30 C atoms
or
an aryl group having 6 to 12 C atoms, where the aryl group having 6 to 12 C atoms may be substituted by alkyl, vinyl, OH, Oalkyl, $NH_2$, NHalkyl, $N(alkyl)_2$, C(O)alkyl, O—C(O)alkyl and/or C(O)Oalkyl or
a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl, and alkyl denotes a straight-chain or branched alkyl group having 1 to 30 C atoms,
and/or salts, tautomers, stereoisomers and/or solvates thereof, including mixtures thereof in all ratios, as self-tanning substance.

2. A method for enhancing the tanning effect of a preparation comprising dihydroxyacetone and/or a mixture of self-tanning substances comprising dihydroxyacetone, comprising enhancing said tanning effect by combining said preparation with at least one compound of the formula

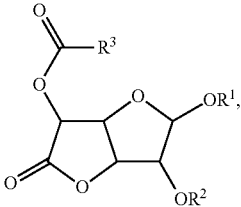

where
$R^1$ and $R^2$ each, independently of one another, denote
a straight-chain or branched alkyl group having 1 to 30 C atoms,
and
either $R^1$ or $R^2$ may denote H,
or
$R^1$ and $R^2$ together form an unsubstituted or substituted five-membered ring, which may be substituted
a) by at least one straight-chain or branched alkyl group having 1 to 30 C atoms and/or
b) by at least one aryl group having 6 to 12 C atoms,
where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl,
$R^3$ denotes a straight-chain or branched alkyl group having 1 to 30 C atoms
or
an aryl group having 6 to 12 C atoms, where the aryl group having 6 to 12 C atoms may be substituted by alkyl, vinyl, OH, Oalkyl, $NH_2$, NHalkyl, $N(alkyl)_2$, C(O)alkyl, O—C(O)alkyl and/or C(O)Oalkyl or
a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl
and
alkyl denotes a straight-chain or branched alkyl group having 1 to 30 C atoms,
and/or salts, tautomers, stereoisomers and/or solvates thereof, including mixtures thereof in all ratios.

3. A method for modulating the effect of a preparation comprising dihydroxyacetone or a mixture of self-tanning agents comprising dihydroxyacetone enabling said preparation to achieve a more natural hue on skin when applied, by combining said preparation with at least one compound of the formula I

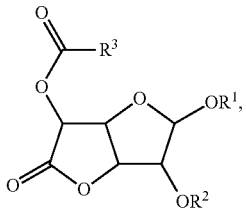

where
R¹ and R² each, independently of one another, denote a straight-chain or branched alkyl group having 1 to 30 C atoms,
and
either R¹ or R² may denote H,
or
R¹ and R² together form an unsubstituted or substituted five-membered ring, which may be substituted
a) by at least one straight-chain or branched alkyl group having 1 to 30 C atoms and/or
b) by at least one aryl group having 6 to 12 C atoms,
where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl,
$R^3$ denotes a straight-chain or branched alkyl group having 1 to 30 C atoms
or
an aryl group having 6 to 12 C atoms, where the aryl group having 6 to 12 C atoms may be substituted by alkyl, vinyl, OH, Oalkyl, $NH_2$, NHalkyl, $N(alkyl)_2$, C(O)alkyl, O—C(O)alkyl and/or C(O)Oalkyl or
a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl
and
alkyl denotes a straight-chain or branched alkyl group having 1 to 30 C atoms,
and/or salts, tautomers, stereoisomers and/or solvates thereof, including mixtures thereof in all ratios.

4. A method for achieving a contrast-reducing effect on the skin when applying a preparation comprising a skin whitener, comprising achieving a contrast-reducing effect when said preparation is applied to the skin, by combining said preparation with at least one compound of the formula I

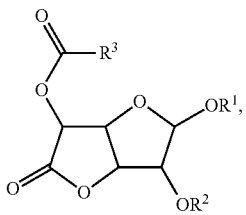

where
R¹ and R² each, independently of one another, denote a straight-chain or branched alkyl group having 1 to 30 C atoms,
and
either R¹ or R² may denote H,
or
R¹ and R² together form an unsubstituted or substituted five-membered ring, which may be substituted
a) by at least one straight-chain or branched alkyl group having 1 to 30 C atoms and/or
b) by at least one aryl group having 6 to 12 C atoms,
where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl,
$R^3$ denotes a straight-chain or branched alkyl group having 1 to 30 C atoms
or
an aryl group having 6 to 12 C atoms, where the aryl group having 6 to 12 C atoms may be substituted by alkyl, vinyl, OH, Oalkyl, $NH_2$, NHalkyl, $N(alkyl)_2$, C(O)alkyl, O—C(O)alkyl and/or C(O)Oalkyl or
a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl
and
alkyl denotes a straight-chain or branched alkyl group having 1 to 30 C atoms,
and/or salts, tautomers, stereoisomers and/or solvates thereof, including mixtures thereof in all ratios, as contrast-reduction agent.

5. A method of coloring keratin fibers, comprising applying to said fibers at least one compound of the formula I

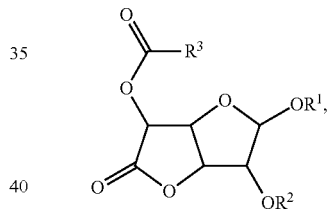

where
R¹ and R² each, independently of one another, denote a straight-chain or branched alkyl group having 1 to 30 C atoms,
and
either R¹ or R² may denote H,
or
R¹ and R² together form an unsubstituted or substituted five-membered ring, which may be substituted
a) by at least one straight-chain or branched alkyl group having 1 to 30 C atoms and/or
b) by at least one aryl group having 6 to 12 C atoms,
where the aryl group having 6 to 12 C atoms may be substituted by alkyl, OH, Oalkyl, $NH_2$, NHalkyl, $N(alkyl)_2$, C(O)alkyl, O—C(O)alkyl and/or C(O)Oalkyl,
$R^3$ denotes a straight-chain or branched alkyl group having 1 to 30 C atoms
or
an aryl group having 6 to 12 C atoms, where the aryl group having 6 to 12 C atoms may be substituted by alkyl, vinyl, OH, Oalkyl, $NH_2$, NHalkyl, $N(alkyl)_2$, C(O)alkyl, O—C(O)alkyl and/or C(O)Oalkyl or
a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, NH$_2$, NHalkyl, N(alkyl)$_2$, C(O)alkyl, O—C(O)alkyl and/or C(O)Oalkyl
and
alkyl denotes a straight-chain or branched alkyl group having 1 to 30 C atoms,
and/or salts, tautomers, stereoisomers and/or solvates thereof, including mixtures thereof in all ratios, for colouring keratin-containing fibres.

6. The method according to claim 1, wherein R$^1$ and R$^2$ in the compound of the formula I together form a five-membered ring, which is substituted by two straight-chain or branched alkyl groups having 1 to 30 C atoms which are independent of one another.

7. The method according to claim 1, wherein the compound of the formula I corresponds to the compound of the formula IA,

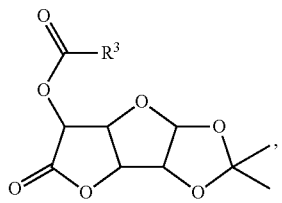

where
R$^3$ denotes a straight-chain or branched alkyl group having 1 to 30 C atoms
or
an aryl group having 6 to 12 C atoms, where the aryl group having 6 to 12 C atoms may be substituted by alkyl, vinyl, OH, Oalkyl, NH$_2$, NHalkyl, N(alkyl)$_2$, C(O)alkyl, O—C(O)alkyl and/or C(O)Oalkyl or
a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, NH$_2$, NHalkyl, N(alkyl)$_2$, C(O)alkyl, O—C(O)alkyl and/or C(O)Oalkyl
and
alkyl denotes a straight-chain or branched alkyl group having 1 to 30 C atoms.

8. The method according to claim 1, wherein the compound of the formula I is a compound of formula (Ia) to (Iq)

(Ia)
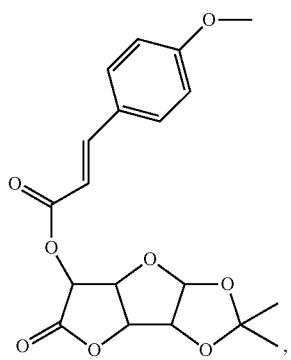

(Ib)
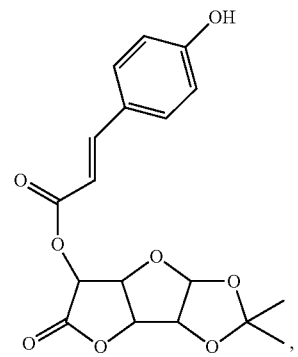

(Ic)
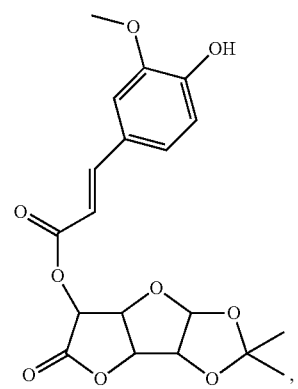

(Id)
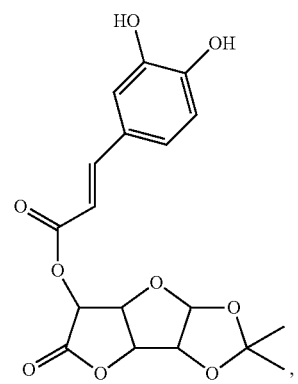

(Ie)
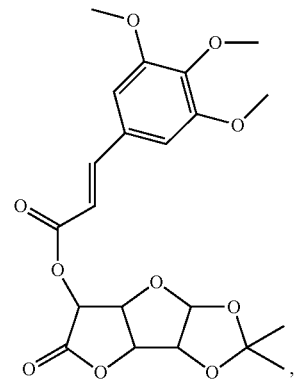

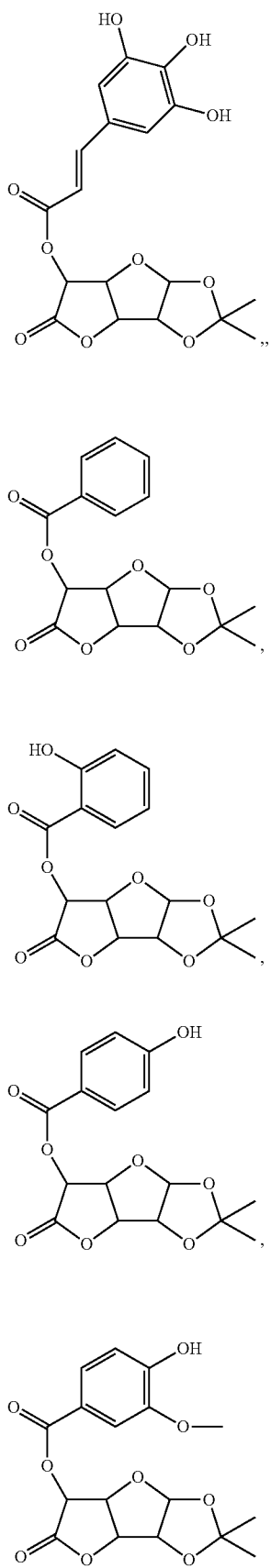
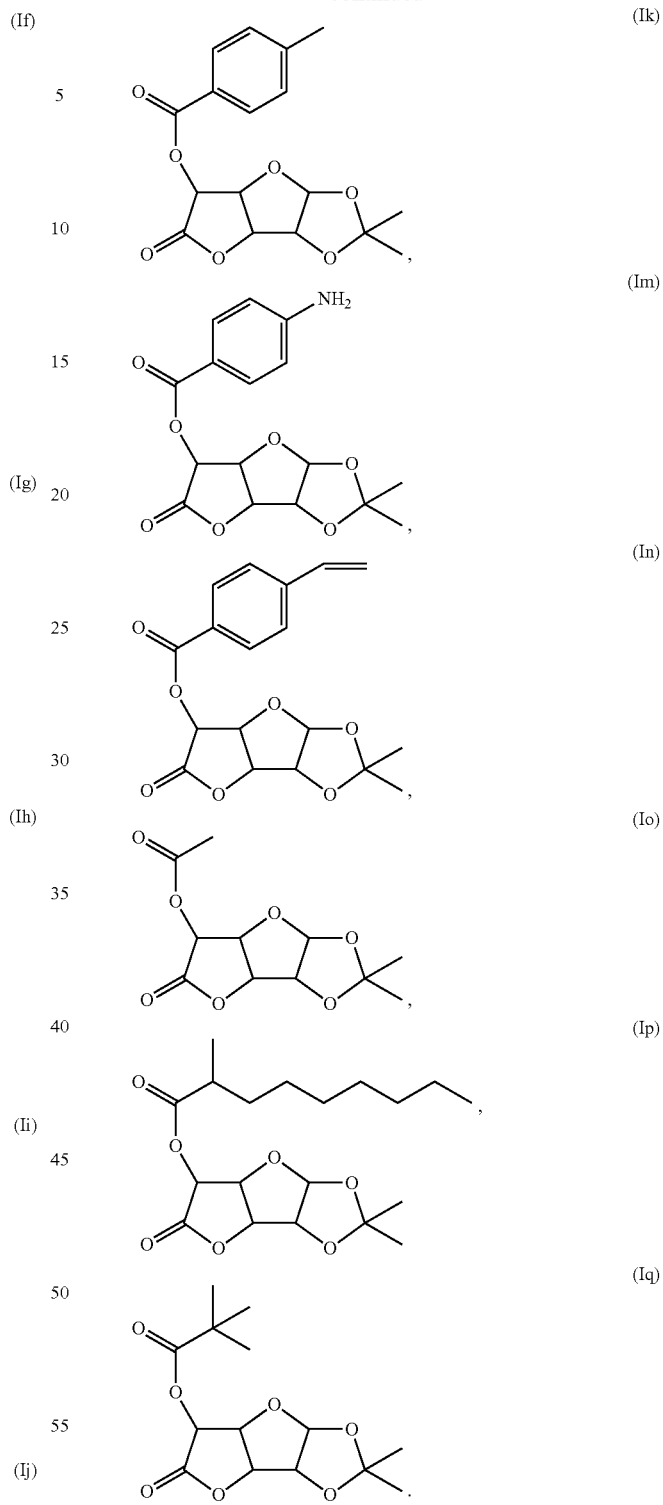

9. A topical preparation comprising at least one compound of the formula I according to claim 1 and/or salts, tautomers, stereoisomers and/or solvates thereof, including mixtures thereof in all ratios, and a topical carrier suitable for cosmetic, pharmaceutical, dermatological preparation.

10. A process for the preparation of a preparation according to claim 9, comprising mixing at least one compound of the formula I together with at least one vehicle which is suitable for cosmetic, pharmaceutical, dermatological preparations and optionally assistants and/or fillers or self-tanning substances.

11. The preparation according to claim 9, further comprising a direct dye or at least one oxidation dye precursor.

12. A compound of formula IB

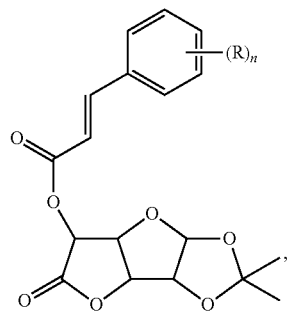

(IB)

where n denotes 0, 1, 2, 3, 4 or 5 and

R in each case, independently of one another, denotes alkyl, OH, Oalkyl, $NH_2$, NHalkyl, $N(alkyl)_2$, C(O)alkyl, O—C(O)alkyl and/or C(O)Oalkyl and alkyl denotes a straight-chain or branched alkyl group having 1 to 30 C atoms and/or salts, tautomers, stereoisomers and/or solvates thereof including mixtures thereof in all ratios.

13. The compound according to claim 12, of the formulae (Ia)

(Ib)

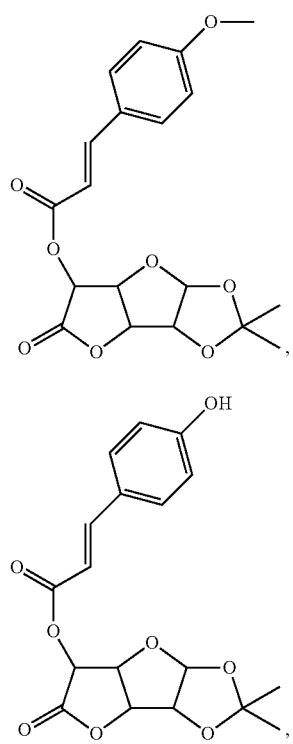

(Ic)

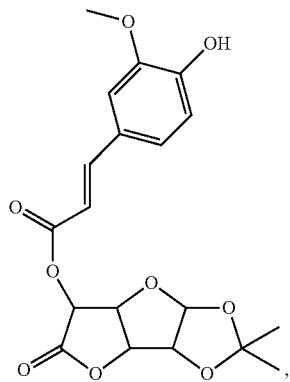

(Id)

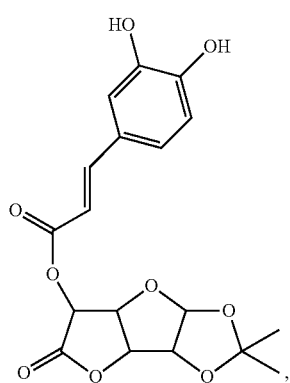

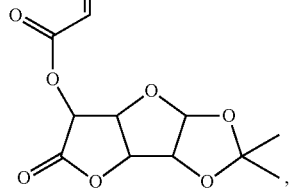

(Ie)

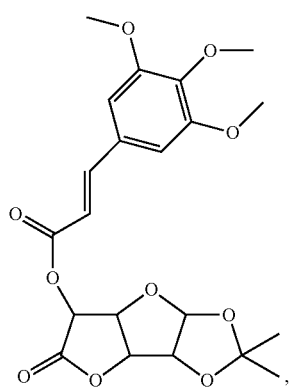

(If)

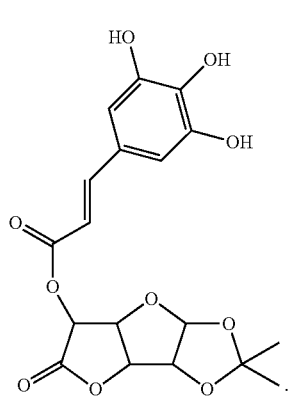

14. A process for the preparation of compounds of the formula IB according to claim 12, comprising reacting an active ester, an acid chloride, an acid bromide or methyl ester of the acid of the formula IV,

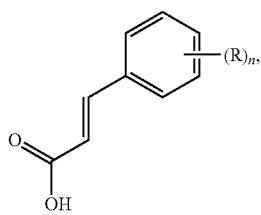

with a compound of the formula III

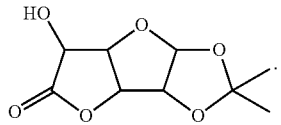

15. The method according to claim 2, wherein $R^1$ and $R^2$ in the compound of the formula I together form a five-membered ring, which is substituted by two straight-chain or branched alkyl groups having 1 to 30 C atoms which are independent of one another.

16. The method according to claim 3, wherein $R^1$ and $R^2$ in the compound of the formula I together form a five-membered ring, which is substituted by two straight-chain or branched alkyl groups having 1 to 30 C atoms which are independent of one another.

17. The method according to claim 4, wherein $R^1$ and $R^2$ in the compound of the formula I together form a five-membered ring, which is substituted by two straight-chain or branched alkyl groups having 1 to 30 C atoms which are independent of one another.

18. The method according to claim 5, wherein $R^1$ and $R^2$ in the compound of the formula I together form a five-membered ring, which is substituted by two straight-chain or branched alkyl groups having 1 to 30 C atoms which are independent of one another.

19. The method according to claim 2, wherein the compound of the formula I corresponds to the compound of the formula IA,

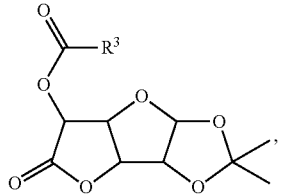

where
$R^3$ denotes a straight-chain or branched alkyl group having 1 to 30 C atoms
or
an aryl group having 6 to 12 C atoms, where the aryl group having 6 to 12 C atoms may be substituted by alkyl, vinyl, OH, Oalkyl, $NH_2$, NHalkyl, N(alkyl)$_2$, C(O)alkyl, O—C(O)alkyl and/or C(O)Oalkyl or
a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, $NH_2$, NHalkyl, N(alkyl)$_2$, C(O)alkyl, O—C(O)alkyl and/or C(O)Oalkyl
and
alkyl denotes a straight-chain or branched alkyl group having 1 to 30 C atoms.

20. The method according to claim 3, wherein the compound of the formula I corresponds to the compound of the formula IA,

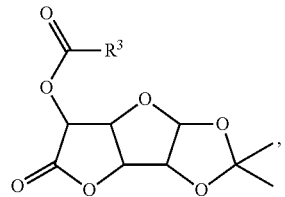

where
$R^3$ denotes a straight-chain or branched alkyl group having 1 to 30 C atoms
or
an aryl group having 6 to 12 C atoms, where the aryl group having 6 to 12 C atoms may be substituted by alkyl, vinyl, OH, Oalkyl, $NH_2$, NHalkyl, N(alkyl)$_2$, C(O)alkyl, O—C(O)alkyl and/or C(O)Oalkyl or
a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, $NH_2$, NHalkyl, N(alkyl)$_2$, C(O)alkyl, O—C(O)alkyl and/or C(O)Oalkyl
and
alkyl denotes a straight-chain or branched alkyl group having 1 to 30 C atoms.

21. The method according to claim 4, wherein the compound of the formula I corresponds to the compound of the formula IA,

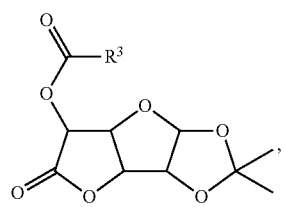

where
$R^3$ denotes a straight-chain or branched alkyl group having 1 to 30 C atoms
or
an aryl group having 6 to 12 C atoms, where the aryl group having 6 to 12 C atoms may be substituted by alkyl, vinyl, OH, Oalkyl, $NH_2$, NHalkyl, N(alkyl)$_2$, C(O)alkyl, O—C(O)alkyl and/or C(O)Oalkyl or
a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, $NH_2$, NHalkyl, N(alkyl)$_2$, C(O)alkyl, O—C(O)alkyl and/or C(O)Oalkyl and
alkyl denotes a straight-chain or branched alkyl group having 1 to 30 C atoms.

22. The method according to claim 5, wherein the compound of the formula I corresponds to the compound of the formula IA,

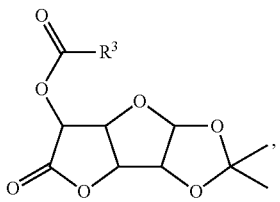
(IA)

where
R³ denotes a straight-chain or branched alkyl group having 1 to 30 C atoms
or
an aryl group having 6 to 12 C atoms, where the aryl group having 6 to 12 C atoms may be substituted by alkyl, vinyl, OH, Oalkyl, NH₂, NHalkyl, N(alkyl)₂, C(O)alkyl, O—C(O)alkyl and/or C(O)Oalkyl or
a straight-chain or branched alkenyl group having 2 to 30 C atoms, which may be substituted by an aryl group having 6 to 12 C atoms, where the aryl group having 6 to 12 C atoms may be substituted by alkyl, OH, Oalkyl, NH₂, NHalkyl, N(alkyl)₂, C(O)alkyl, O—C(O)alkyl and/or C(O)Oalkyl
and
alkyl denotes a straight-chain or branched alkyl group having 1 to 30 C atoms.

23. The method according to claim 2, wherein the compound of the formula I is a compound of formula (Ia) to (Iq)

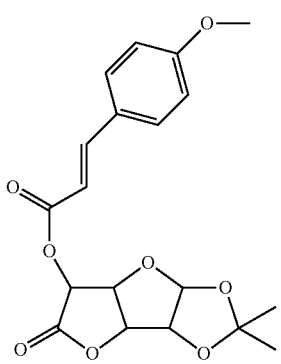
(Ia)

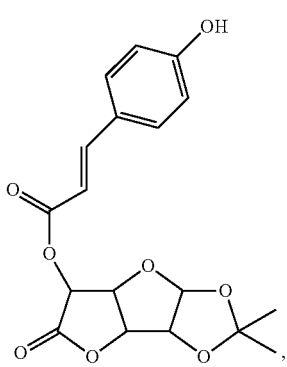
(Ib)

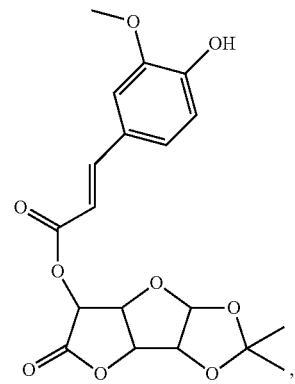
(Ic)

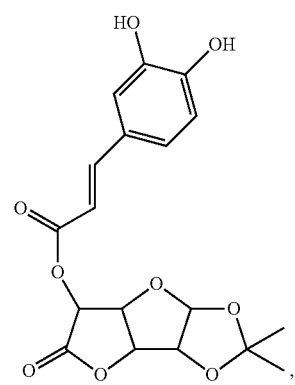
(Id)

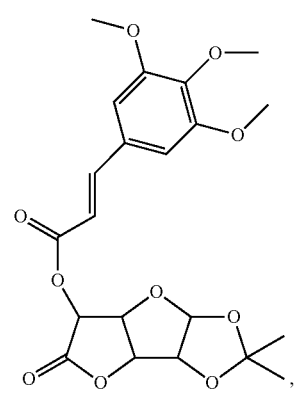
(Ie)

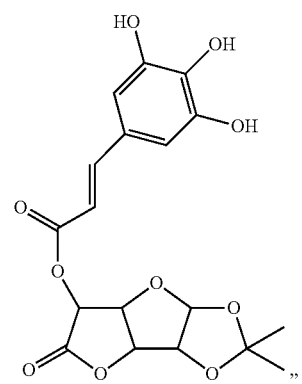
(If)

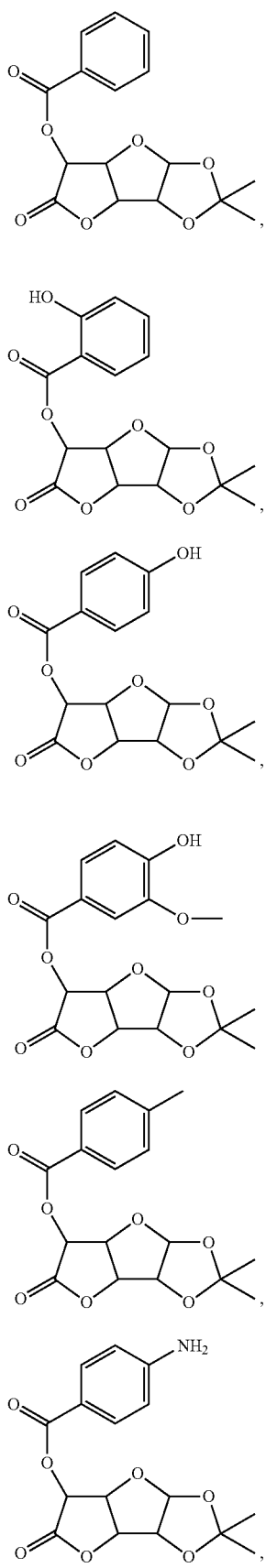
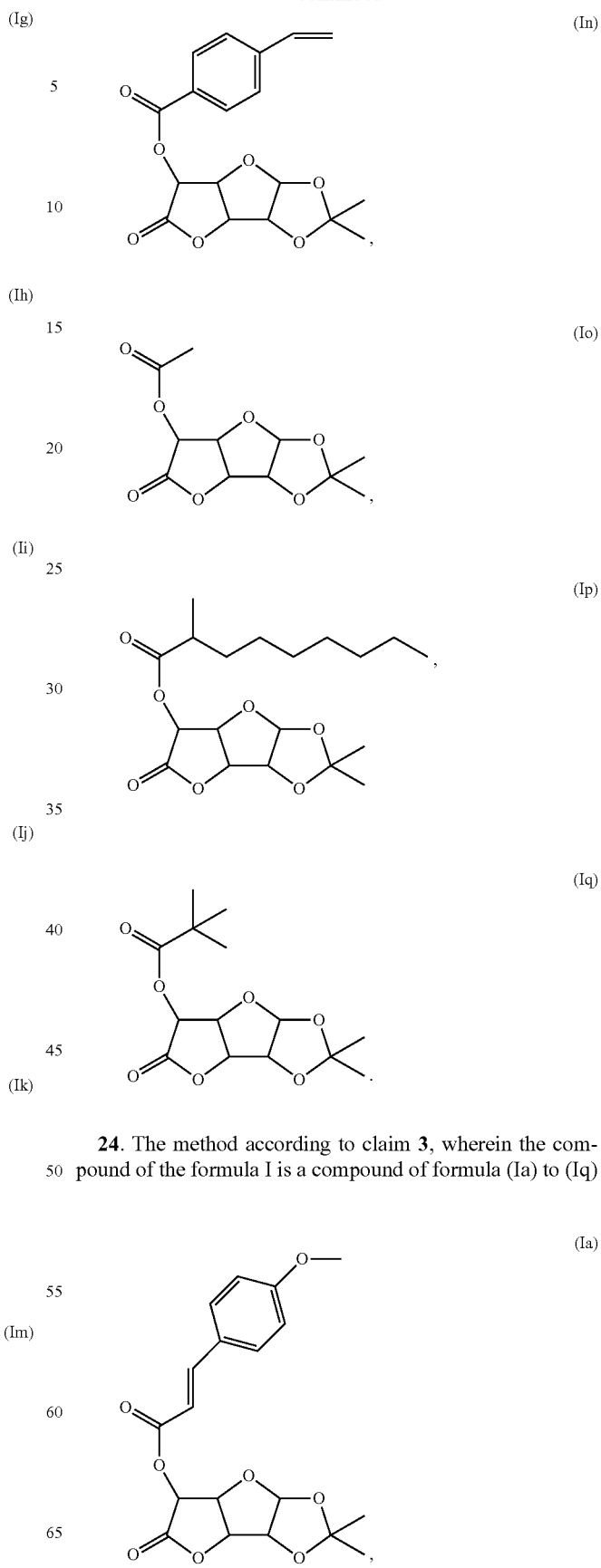
24. The method according to claim 3, wherein the compound of the formula I is a compound of formula (Ia) to (Iq)
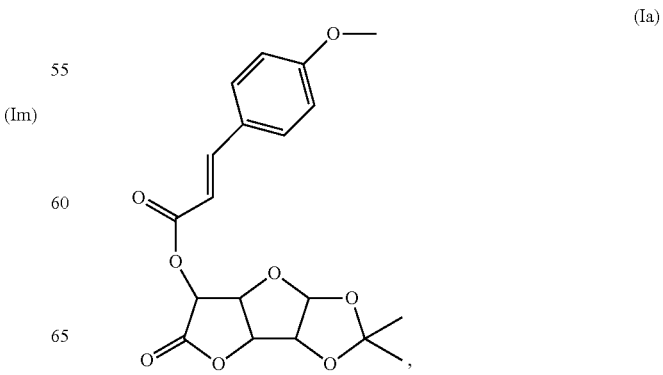

(Ib)
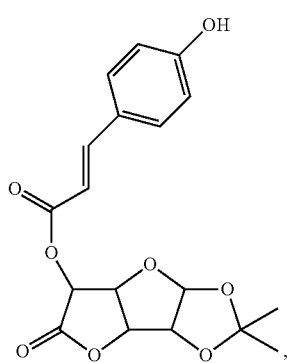
(Ic)
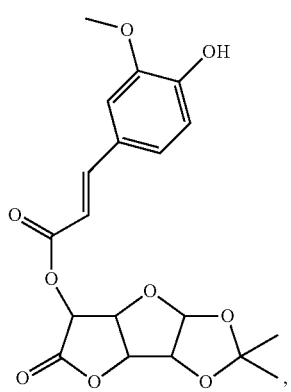
(Id)
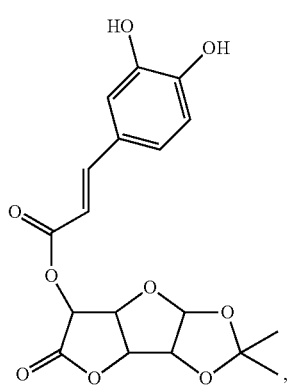
(Ie)
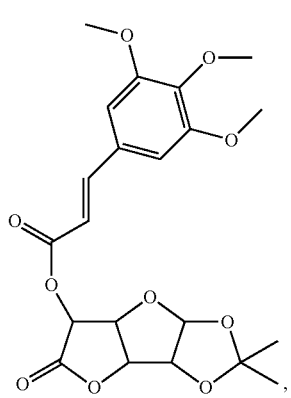
(If)
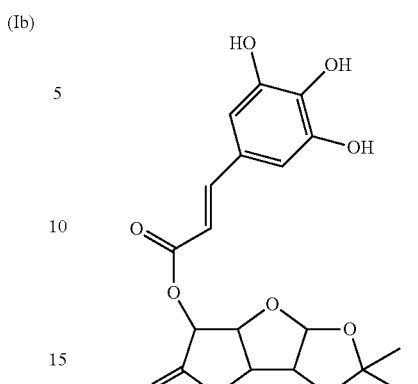
(Ig)
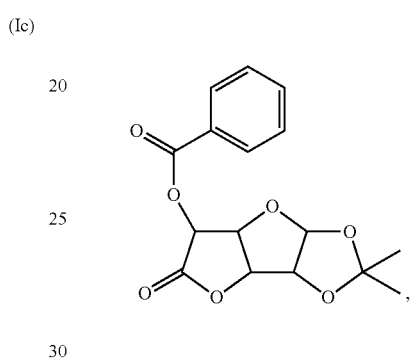
(Ih)
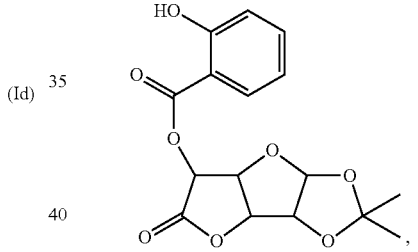
(Ii)
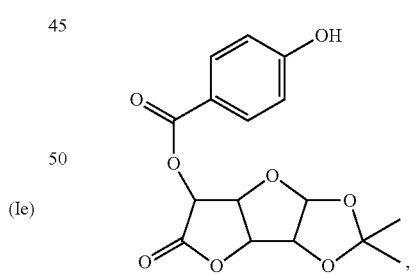
(Ij)
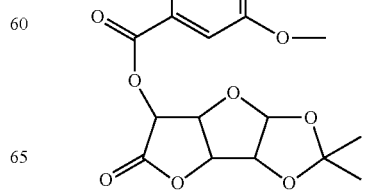

-continued
(Ik)
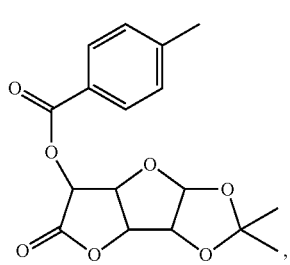
(Im)
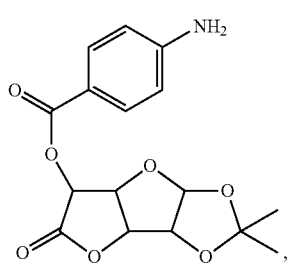
(In)
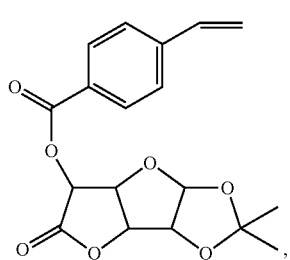
(Io)
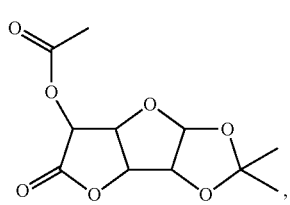
(Ip)
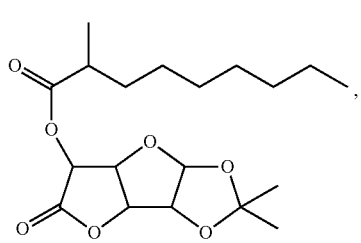
(Iq)
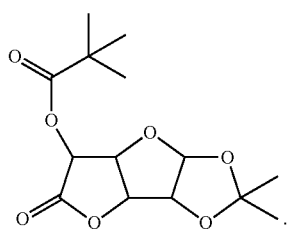
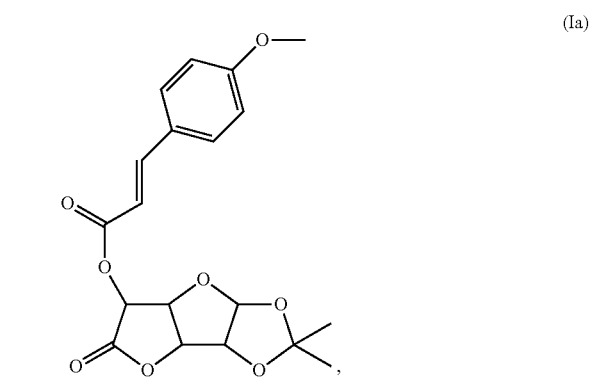
25. The method according to claim 4, wherein the compound of the formula I is a compound of formula (Ia) to (Iq)

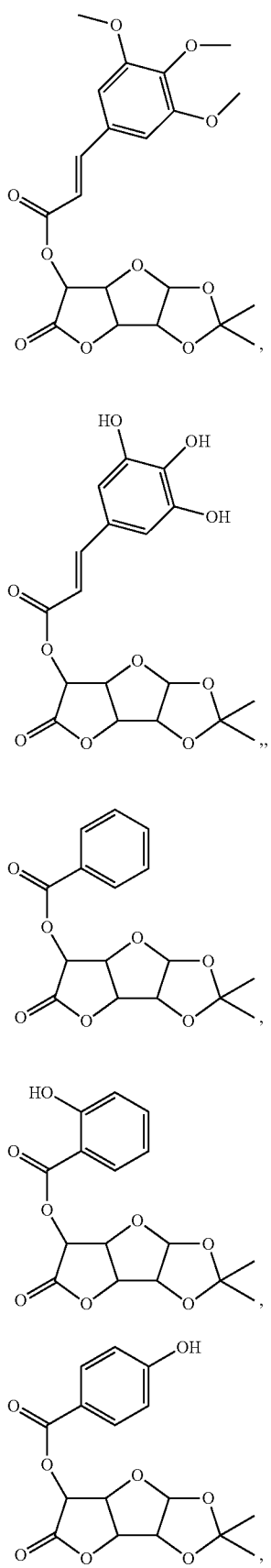
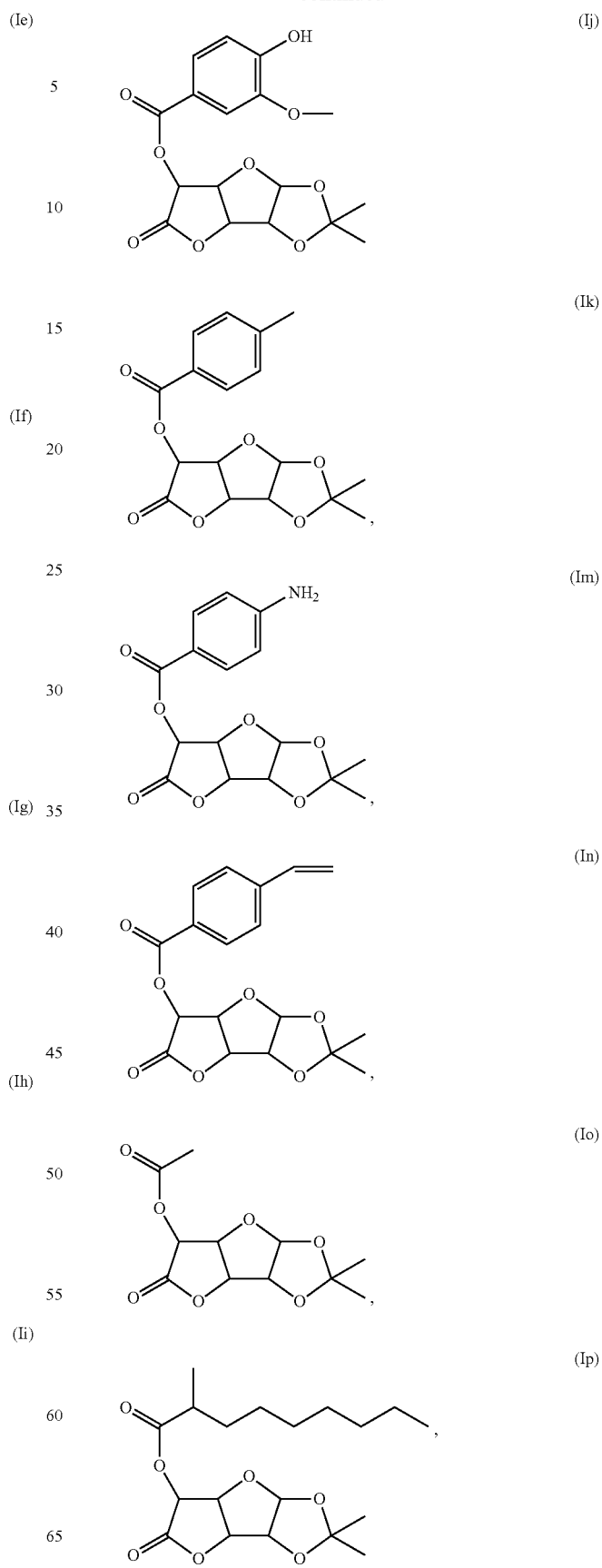

75
-continued
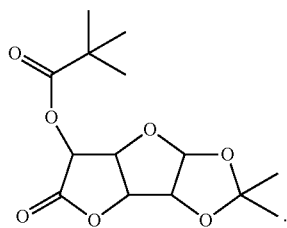
(Iq)
26. The method according to claim 5, wherein the compound of the formula I is a compound of formula (Ia) to (Iq)
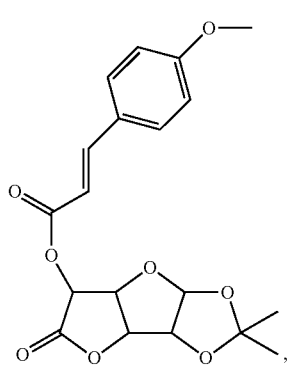
(Ia)
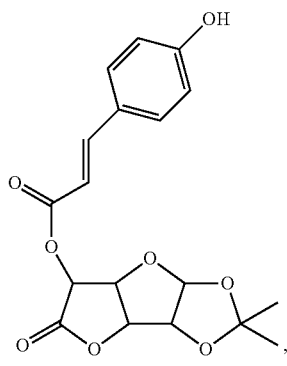
(Ib)
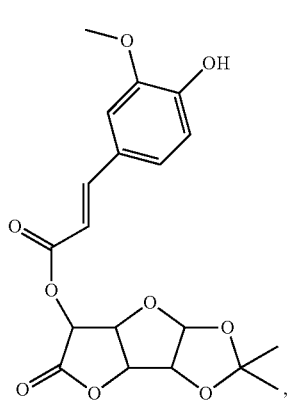
(Ic)
76
-continued
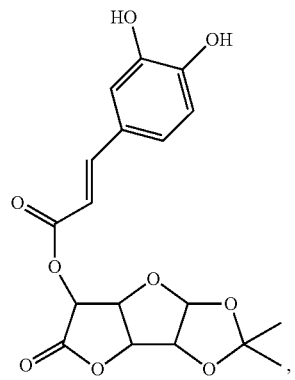
(Id)
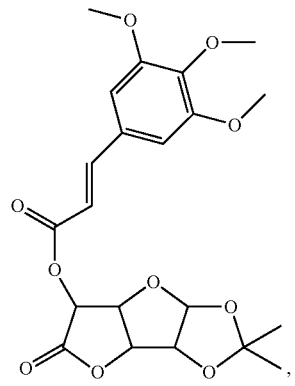
(Ie)
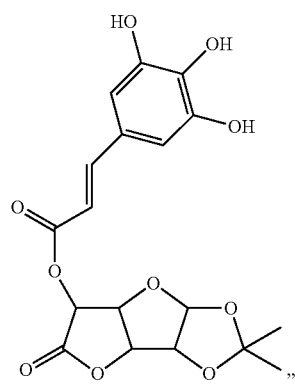
(If)
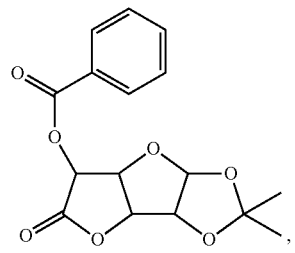
(Ig)

-continued
(Ih) 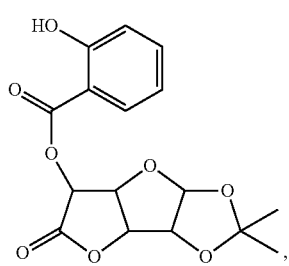
(Ii) 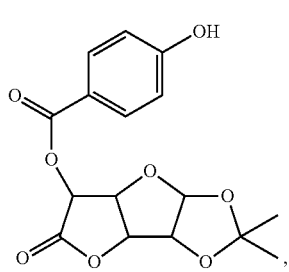
(Ij) 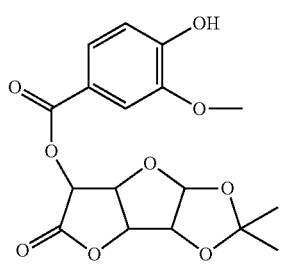
(Ik) 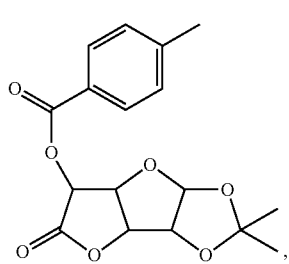
-continued
(Im) 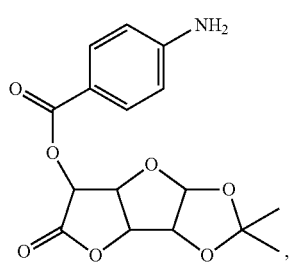
(In) 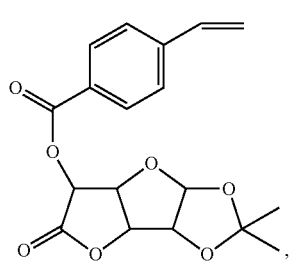
(Io) 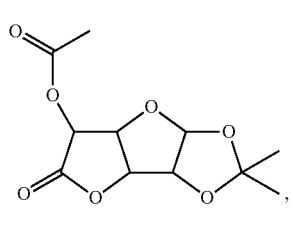
(Ip) 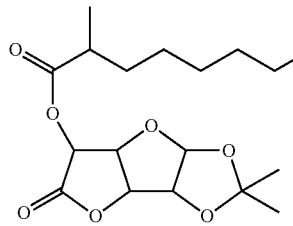
(Iq) 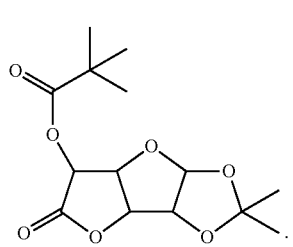
* * * * *